(12) United States Patent
Buyse et al.

(10) Patent No.: US 11,306,139 B2
(45) Date of Patent: Apr. 19, 2022

(54) GLYCOSYLATED IMMUNOGLOBULIN SINGLE VARIABLE DOMAINS

(71) Applicant: Ablynx N.V., Ghent-Zwijnaarde (BE)

(72) Inventors: Marie-Ange Buyse, Merelbeke (BE); Carlo Boutton, Wielsbeke (BE)

(73) Assignee: Ablynx N.V., Ghent-Zwijnaarde (BE)

( * ) Notice: Subject to any disclaimer, the term of this patent is extended or adjusted under 35 U.S.C. 154(b) by 237 days.

(21) Appl. No.: 15/554,744

(22) PCT Filed: Mar. 18, 2016

(86) PCT No.: PCT/EP2016/055947
§ 371 (c)(1),
(2) Date: Aug. 31, 2017

(87) PCT Pub. No.: WO2016/150845
PCT Pub. Date: Sep. 29, 2016

(65) Prior Publication Data
US 2018/0044407 A1 Feb. 15, 2018

Related U.S. Application Data

(60) Provisional application No. 62/135,968, filed on Mar. 20, 2015.

(51) Int. Cl.
*A61K 39/00* (2006.01)
*C07K 16/00* (2006.01)
*C12P 21/08* (2006.01)
*C07K 16/18* (2006.01)

(52) U.S. Cl.
CPC .......... *C07K 16/18* (2013.01); *C07K 2317/40* (2013.01); *C07K 2317/41* (2013.01); *C07K 2317/56* (2013.01); *C07K 2317/567* (2013.01); *C07K 2317/569* (2013.01)

(58) Field of Classification Search
None
See application file for complete search history.

(56) References Cited

U.S. PATENT DOCUMENTS

| | | | |
|---|---|---|---|
| 5,041,376 A | 8/1991 | Gething et al. | |
| 9,371,374 B2* | 6/2016 | Ziemann | G01N 33/5767 |
| 2011/0182897 A1* | 7/2011 | Hultberg | A61P 31/14 424/134.1 |
| 2012/0151610 A1* | 6/2012 | Craig | C07K 16/2896 800/6 |
| 2013/0209458 A1* | 8/2013 | Goletz | A61P 43/00 424/133.1 |
| 2014/0322129 A1* | 10/2014 | Leong | C07K 16/2827 424/1.49 |

FOREIGN PATENT DOCUMENTS

| | | | |
|---|---|---|---|
| WO | WO 2000/05389 A2 | 2/2000 | |
| WO | WO-2008020079 A1 * | 2/2008 | ............ C12N 15/81 |
| WO | WO-2011051327 A2 * | 5/2011 | ............ C07K 16/00 |

OTHER PUBLICATIONS

Ablynx, "Understanding Nanobodies," available online at https://www.ablynx.com/technology-innovation/understanding-nanobodies/, 2 pages (2015) (Year: 2015).*
Honegger et al., J. Mol. Biol. 309:657-670 (2001) (Year: 2001).*
UniProt, Glycosylation, available online at https://www.uniprot.org/help/carbohyd, 4 pages (first available 2014 and last updated 2018) (Year: 2014).*
Merriam-Webster, "Polypeptide," available online at https://www.merriam-webster.com/dictionary/polypeptide, 16 pages (accessed on Nov. 1, 2019) (Year: 2019).*
Mitchell et al., Proteins 86:697-706 (2018) (Year: 2018).*
Holt et al., TRENDS in Biotechnology, 21:484-490 (2003) (Year: 2003).*
Wesolowski et al., Med. Microbiol. Immunol. 198:157-174 (2009) (Year: 2009).*
Vincke et al., Introduction to Heavy Chain Antibodies and Derived Nanobodies, in Methods in Molecular Biology, vol. 911, pp. 15-26, 2012 (Year: 2012).*
Wilton et al., ACS Synth. Biol. 7:2480-2484 (2018) (Year: 2018).*
GenBank Database, Accession No. BAD00453, 2 pages (first available 2003) (Year: 2003).*

(Continued)

*Primary Examiner* — Thea D' Ambrosio
(74) *Attorney, Agent, or Firm* — Wolf, Greenfield & Sacks, P.C.

(57) ABSTRACT

The present invention relates to glycosylated immunoglobulin variable domains, and in particular to glycosylated immunoglobulin single variable domains (the latter also being referred to herein by means of the abbreviation "ISF" or "ISVD"). The present invention relates to glycosylated immunoglobulin heavy-chain variable domains (also referred to herein as "VH domains"), and in particular to glycosylated immunoglobulin heavy-chain ISVD's. The invention in particular relates to immunoglobulin (single) variable domains that are glycosylated in such a way that the binding of said immunoglobulin (single) variable domains by so-called "pre-existing antibodies" is prevented and/or reduced (i.e. partially or essentially completely) compared to the same immunoglobulin (single) variable domain without the glycosylation of the invention being present. For example, the present invention relates to heavy-chain immunoglobulin variable domain, which contains a glycosylation site such that the amino acid residue at one of positions 10, 11, 12, 13, 14, 39, 40, 41, 42, 87, 89, 108, 110, 112, 113 or 114, and in particular one of positions 11, 13, 87, 89, 108, 110, 112, 113 or 114 (numbering according to Kabat) is or can be glycosylated.

24 Claims, 15 Drawing Sheets
Specification includes a Sequence Listing.

(56) References Cited

OTHER PUBLICATIONS

Spiro, Protein glycosylation: nature, distribution, enzymatic formation, and disease implications of glycopeptide bonds. Glycobiology. 2002;12(4):43R-56R. doi:10.1093/glycob/12.4.43r.

Decanniere et al., A single-domain antibody fragment in complex with RNase A: non-canonical loop structures and nanomolar affinity using two CDR loops. Structure. Apr. 15, 1999;7(4):361-70. doi: 10.1016/s0969-2126(99)80049-5.

Desmyter et al., Crystal structure of a camel single-domain VH antibody fragment in complex with lysozyme. Nat Struct Biol. Sep. 1996;3(9):803-11. doi: 10.1038/nsb0996-803.

Johnson et al., Kabat database and its applications: 30 years after the first variability plot. Nucleic Acids Res. Jan. 1, 2000;28(1):214-8. doi: 10.1093/nar/28.1.214.

Martin, Chapter 3: Protein Sequence and Structure Analysis of Antibody Variable Domains. Antibody Eng. 2010;2:33-51.

Muyldermans, Single domain camel antibodies: current status. J Biotechnol. Jun. 2001;74(4):277-302. doi: 10.1016/s1389-0352(01)00021-6.

Riechmann et al., Single domain antibodies: comparison of camel VH and camelised human VH domains. J Immunol Methods. Dec. 10, 1999;231(1-2):25-38. doi: 10.1016/s0022-1759(99)00138-6.

Spinelli et al., The crystal structure of a llama heavy chain variable domain. Nat Struct Biol. Sep. 1996;3(9):752-7. doi: 10.1038/nsb0996-752.

\* cited by examiner

Figure 1

| Numbering according to Kabat (VH) | Numbering according to Chothia (VH) | Aho numbering | IMGT |
|---|---|---|---|
| 11 | 11 | 12 | 12 |
| 14 | 14 | 15 | 15 |
| 41 | 41 | 48 | 46 |
| 42 | 42 | 49 | 47 |
| 87 | 87 | 101 | 99 |
| 89 | 89 | 103 | 101 |
| 108 | 108 | 144 | --- |
| 109 | 109 | 145 | --- |
| 110 | 110 | 146 | --- |
| 111 | 111 | 145 | --- |
| 112 | 112 | 148 | --- |

Source: http://www.bioc.uzh.ch/plueckthun/antibody/Numbering/NumFrame.html

Figure 2

| Pos. | Amino acid residue(s): | | $V_{HH}$ Ent. | $V_{HH}$ Var. |
|---|---|---|---|---|
| | Human $V_H3$ | Camelid $V_{HH}$'s | | |
| 103 | W | Hallmark residue: W, R, G, S, K, A, M, Y, L, F, T, N, V, Q, P, E, C; preferably W | 0,54 | 6 |
| 104 | G | Hallmark residue: G, A, S, T, D, P, N, E, C, L; preferably G | 0,13 | 3 |
| 105 | Q, R | Q, K, H, R, P, E, L, T, N, S, V, A, M, G | 0,52 | 5 |
| 106 | G | G, R, E | 0 | 1 |
| 107 | T | T, Q, L, A, S, N, R, V, D | 0,24 | 3 |
| 108 | L | Hallmark residue: Q, L, R, P, E, K, S, T, M, A, H; preferably Q or L | 0,3 | 4 |
| 109 | V | V, I, L | 0 | 1 |
| 110 | T | T, S, N, A, L, F | 0,01 | 1 |
| 111 | V | V, I, A | 0,01 | 1 |
| 112 | S | S, T, P, F, A | 0,01 | 1 |
| 113 | S | S, T, A, L, P, F, E, V | 0,04 | 1 |

Figure 3

| Pos. | NXT or NXS motif at positions 108-110: possible amino acid residue(s) in FR4: | |
|---|---|---|
| | ISV of invention based on human $V_H3$ domain | ISV of invention based on Camelid $V_{HH}$'s |
| 103 | W | W, R, G, S, K, A, M, Y, L, F, T, N, V, Q, P, E, C; preferably W |
| 104 | G | G, A, S, T, D, P, N, E, C, L; preferably G |
| 105 | Q, R | Q, K, H, R, P, E, L, T, N, S, V, A, M, G |
| 106 | G | G, R, E |
| 107 | T | T, Q, I, A, S, N, R, V, D |
| 108 | N | N |
| 109 | X[(1)] | X[(1)] |
| 110 | T or S | T or S |
| 111 | V | V, I, A |
| 112 | S | S, T, P, F, A[(3)] |
| 113[(2)] | S | S, T, A, L, P, F, E, V |

(1) X can be any suitable amino acid residue, but is preferably V, I or, L.
(2) Optionally, an ISV of the invention can contain a C-terminal extension (X)n, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I).
(3) Can also be a K or Q mutation, as described in the copending US priority applications entitled "Improved immunoglobulin variable domains" mentioned on page 6 of the description

Figure 4

| Pos. | NXT or NXS motif at positions 110-112: possible amino acid residue(s) in FR4: | |
|---|---|---|
| | *ISV of invention based on human V$_H$3 domain* | *ISV of invention based on Camelid V$_{HH}$'s* |
| 103 | W | W, R, G, S, K, A, M, Y, L, F, T, N, V, Q, P, E, C; preferably W |
| 104 | G | G, A, S, T, D, P, N, E, C, L; preferably G |
| 105 | Q, R | Q, K, H, R, P, E, L, T, N, S, V, A, M, G |
| 106 | G | G, R, E |
| 107 | T | T, Q, I, A, S, N, R, V, D |
| 108 | L | Q, L, R, P, E, K, S, T, M, A, H; preferably Q or L |
| 109 | V | V, I, L |
| 110 | N | N |
| 111 | X$^{(1)}$ | X$^{(1)}$ |
| 112 | T or S | T or S |
| 113$^{(2)}$ | S | S, T, A, L, P, F, E, V |
| (1) X can be any suitable amino acid residue, but is preferably V, I or A | | |
| (2) Optionally, an ISV of the invention can contain a C-terminal extension (X)$_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I). | | |

Figure 5A

| Pos. | NXT or NXS motif at positions 112-114: possible amino acid residue(s) in FR4: | |
|---|---|---|
| | *ISV of invention based on human $V_H3$ domain* | *ISV of invention based on Camelid $V_{HH}$'s* |
| 103 | W | W, R, G, S, K, A, M, Y, I, F, T, N, V, Q, P, E, C; preferably W |
| 104 | G | G, A, S, T, D, P, N, E, C, L; preferably G |
| 105 | Q, R | Q, K, H, R, P, E, L, T, N, S, V, A, M, G |
| 106 | G | G, R, E |
| 107 | T | T, Q, I, A, S, N, R, V, D |
| 108 | L | Q, L, R, P, E, K, S, T, M, A, H; preferably Q or L |
| 109 | V | V, I, L |
| 110 | T | T, S, N, A, L, F[2] |
| 111 | V | V, I, A |
| 112 | N | N |
| 113 | X[1] | X[1] |
| (114) | T or S | T or S |

(1) X can be any suitable amino acid residue, but is preferably S, T, A, L, P, F, E or V (2) Position 110 can also be a K or Q mutation, as described in the copending US priority applications entitled "*Improved immunoglobulin variable domains*" mentioned on page 6 of the description

Figure 5B

| Pos. | NXT or NXS motif at positions 113-115: possible amino acid residue(s) in FR4: | |
|---|---|---|
| | *ISV of invention based on human $V_H3$ domain* | *ISV of invention based on Camelid $V_{HH}$'s* |
| 103 | W | W, R, G, S, K, A, M, Y, L, F, T, N, V, Q, P, E, C; preferably W |
| 104 | G | G, A, S, T, D, P, N, E, C, L; preferably G |
| 105 | Q, R | Q, K, H, R, P, E, L, T, N, S, V, A, M, G |
| 106 | G | G, R, E |
| 107 | T | T, Q, L, A, S, N, R, V, D |
| 108 | L | Q, L, R, P, E, K, S, T, M, A, H; preferably Q or L |
| 109 | V | V, I, L |
| 110 | T | T, S, N, A, I, F[2] |
| 111 | V | V, I, A |
| 112 | S | S, T, P, F, A[3] |
| 113 | N | N |
| (114) | X[1] | X[1] |
| (115) | T or S | T or S |

(1) X can be any suitable amino acid residue.
(2) Position 110 can also be a K or Q mutation, as described in the copending US priority applications entitled "*Improved immunoglobulin variable domains*" mentioned on page 6 of the description
(3) Position 112 can also be a K or Q mutation, as described in the copending US priority applications entitled "*Improved immunoglobulin variable domains*" mentioned on page 6 of the description

Figure 6

| Pos. | NXT or NXS motif at positions 114-116: possible amino acid residue(s) in FR4: | |
|---|---|---|
| | *ISV of invention based on human V_H3 domain* | *ISV of invention based on Camelid V_HH's* |
| 103 | W | W, R, G, S, K, A, M, Y, L, F, T, N, V, Q, P, E, C; preferably W |
| 104 | G | G, A, S, T, D, P, N, E, C, L; preferably G |
| 105 | Q, R | Q, K, H, R, P, E, L, T, N, S, V, A, M, G |
| 106 | G | G, R, E |
| 107 | T | T, Q, I, A, S, N, R, V, D |
| 108 | L | Q, L, R, P, E, K, S, T, M, A, H; preferably Q or L |
| 109 | V | V, I, L |
| 110 | T | T, S, N, A, I, F$^{(2)}$ |
| 111 | V | V, I, A |
| 112 | S | S, T, P, F, A$^{(3)}$ |
| 113 | S | S, T, A, L, P, F, E, V |
| (114) | N | N |
| (115) | X$^{(1)}$ | X$^{(1)}$ |
| (116) | T or S | T or S |

(1) X can be any suitable amino acid residue.
(2) Position 110 can also be a K or Q mutation, as described in the copending US priority applications entitled *"Improved immunoglobulin variable domains"* mentioned on page 6 of the description
(3) Position 112 can also be a K or Q mutation, as described in the copending US priority applications entitled *"Improved immunoglobulin variable domains"* mentioned on page 6 of the description

Figure 7A

Preferred but non-limiting examples of Framework 4 sequences with glycosylation site at position 108-110

| NXT motif | | NXS motif | |
|---|---|---|---|
| WGQGTNXTVSS | SEQ ID NO: 1 | WGQGTNXSVSS | SEQ ID NO: 10 |
| WGKGTNXTVSS | SEQ ID NO: 2 | WGKGNXSVSS | SEQ ID NO: 11 |
| RGQGTNXTVSS | SEQ ID NO: 3 | RGQGTNXSVSS | SEQ ID NO: 12 |
| WGLGTNXTISS | SEQ ID NO: 4 | WGLGTNXSISS | SEQ ID NO: 13 |
| GSQGTNXTVSS | SEQ ID NO: 5 | GSQGTNXSVSS | SEQ ID NO: 14 |
| LRGGTNXTVSS | SEQ ID NO: 6 | LRGGTNXSVSS | SEQ ID NO: 15 |
| RGQGTNXTVSS | SEQ ID NO: 7 | RGQGTNXSVSS | SEQ ID NO: 16 |
| RSRGINXTVSS | SEQ ID NO: 8 | RSRGINXSVSS | SEQ ID NO: 17 |
| WGKGTNXTVSS | SEQ ID NO: 9 | WGKGTNXSVSS | SEQ ID NO: 18 |

Figure 7B

Preferred but non-limiting examples of Framework 4 sequences with glycosylation site at position 110-112

| NXT motif | | NXS motif | |
|---|---|---|---|
| WGQGTLVNXTS | SEQ ID NO: 19 | WGQGTLVNXSS | SEQ ID NO: 29 |
| WGQGTQVNXTS | SEQ ID NO: 20 | WGQGTQVNXSS | SEQ ID NO: 30 |
| WGKGTLVNXTS | SEQ ID NO: 21 | WGKGTLVNXSS | SEQ ID NO: 31 |
| RGQGTRVNXTS | SEQ ID NO: 22 | RGQGTRVNXSS | SEQ ID NO: 32 |
| WGLGTQVNXTS | SEQ ID NO: 23 | WGLGTQVNXSS | SEQ ID NO: 33 |
| GSQGTQVNXTS | SEQ ID NO: 24 | GSQGTQVNXSS | SEQ ID NO: 34 |
| LRGGTQVNXTS | SEQ ID NO: 25 | LRGGTQVNXSS | SEQ ID NO: 35 |
| RGQGTLVNXTS | SEQ ID NO: 26 | RGQGTLVNXSS | SEQ ID NO: 36 |
| RSRGIQVNXTS | SEQ ID NO: 27 | RSRGIQVNXSS | SEQ ID NO: 37 |
| WGKGTQVNXTS | SEQ ID NO: 28 | RSRGIQVNXSS | SEQ ID NO: 38 |

Figure 7C

Preferred but non-limiting examples of Framework 4 sequences with glycosylation site at position 112-114

| NXT motif | | NXS motif | |
|---|---|---|---|
| WGQGTLVTVNXT | SEQ ID NO: 39 | WGQGTLVTVNXS | SEQ ID NO: 49 |
| WGQGTQVTVNXT | SEQ ID NO: 40 | WGQGTQVTVNXS | SEQ ID NO: 50 |
| WGKGTLVTVNXT | SEQ ID NO: 41 | WGKGTLVTVNXS | SEQ ID NO: 51 |
| RGQGTRVTVNXT | SEQ ID NO: 42 | RGQGTRVTVNXS | SEQ ID NO: 52 |
| WGLGTQVTINXT | SEQ ID NO: 43 | WGLGTQVTINXS | SEQ ID NO: 53 |
| GSQGTQVTVNXT | SEQ ID NO: 44 | GSQGTQVTVNXS | SEQ ID NO: 54 |
| LRGGTQVTVNXT | SEQ ID NO: 45 | LRGGTQVTVNXS | SEQ ID NO: 55 |
| RGQGTLVTVNXT | SEQ ID NO: 46 | RGQGTLVTVNXS | SEQ ID NO: 56 |
| RSRGIQVTVNXT | SEQ ID NO: 47 | RSRGIQVTVNXS | SEQ ID NO: 57 |
| WGKGTQVTVNXT | SEQ ID NO: 48 | WGKGTQVTVNXS | SEQ ID NO: 58 |

Figure 7D

Preferred but non-limiting examples of Framework 4 sequences with glycosylation site at position 113-115

| NXT motif | | NXS motif | |
|---|---|---|---|
| WGQGTLVTVSNXT | SEQ ID NO: 59 | WGQGTLVTVSNXS | SEQ ID NO: 69 |
| WGQGTQVTVSNXT | SEQ ID NO: 60 | WGQGTQVTVSNXS | SEQ ID NO: 70 |
| WGKGILVTVSNXT | SEQ ID NO: 61 | WGKGILVTVSNXS | SEQ ID NO: 71 |
| RGQGTRVTVSNXT | SEQ ID NO: 62 | RGQGTRVTVSNXS | SEQ ID NO: 72 |
| WGLGTQVTISNXT | SEQ ID NO: 63 | WGLGTQVTISNXS | SEQ ID NO: 73 |
| GSQGTQVTVSNXT | SEQ ID NO: 64 | GSQGTQVTVSNXS | SEQ ID NO: 74 |
| LRGGTQVTVSNXT | SEQ ID NO: 65 | LRGGTQVTVSNXS | SEQ ID NO: 75 |
| RGQGTLVTVSNXT | SEQ ID NO: 66 | RGQGTLVTVSNXS | SEQ ID NO: 76 |
| RSRGIQVTVSNXT | SEQ ID NO: 67 | RSRGIQVTVSNXS | SEQ ID NO: 77 |
| WGKGTQVTVSNXT | SEQ ID NO: 68 | WGKGTQVTVSNXS | SEQ ID NO: 78 |

Figure 7E

Preferred but non-limiting examples of Framework 4 sequences with glycosylation site at position 114-116

| NXT motif | | NXS motif | |
|---|---|---|---|
| WGQGTLVTVSSNXT | SEQ ID NO: 79 | WGQGTILVTVSSNXS | SEQ ID NO: 89 |
| WGQGTQVTVSSNXT | SEQ ID NO: 80 | WGQGTQVTVSSNXS | SEQ ID NO: 90 |
| WGKGTLVTVSSNXT | SEQ ID NO: 81 | WGKGTILVTVSSNXS | SEQ ID NO: 91 |
| RGQGTRVTVSSNXT | SEQ ID NO: 82 | RGQGTRVTVSSNXS | SEQ ID NO: 92 |
| WGLGTQVTISSNXT | SEQ ID NO: 83 | WGLGTQVTISSNXS | SEQ ID NO: 93 |
| GSQGTQVTVSSNXT | SEQ ID NO: 84 | GSQGTQVTVSSNXS | SEQ ID NO: 94 |
| LRGGTQVTVSSNXT | SEQ ID NO: 85 | LRGGTQVTVSSNXS | SEQ ID NO: 95 |
| RGQGTLVTVSSNXT | SEQ ID NO: 86 | RGQGTLVTVSSNXS | SEQ ID NO: 96 |
| RSRGIQVTVSSNXT | SEQ ID NO: 87 | RSRGIQVTVSSNXS | SEQ ID NO: 97 |
| WGKGTQVTVSSNXT | SEQ ID NO: 88 | WGKGTQVTVSSNXS | SEQ ID NO: 98 |

Figure 8

| SEQ ID NO: 99 | HHHHHHEVQLVESGGGLVQPGNSLRLSCAASGFTFSSFGMSWVRQAPGKGLEWVSSISGSGSDT LYADSVKGRFTISRDNAKTTLYLQMNSLRPEDTAVYYCTIGGSLSRSSQGTLVTVSS |
| --- | --- |
| SEQ ID NO: 100 | HHHHHHEVQLVESGGGLVQPGNSLRLSCAASGFTFSSFGMSWVRQAPGKGLEWVSSISGSGSDT LYADSVKGRFTISRDNAKTTLYLQMNSLRPEDTAVYYCTIGGSLSRSSQGTNVTVSS |
| SEQ ID NO: 101 | HHHHHHEVQLVESGGGLVQPGNSLRLSCAASGFTFSSFGMSWVRQAPGKGLEWVSSISGSGSDT LYADSVKGRFTISRDNAKTTLYLQMNSLRPNDTAVYYCTIGGSLSRSSQGTLVTVSS |

SEQUENCE LISTING

```
<160> NUMBER OF SEQ ID NOS: 102

<210> SEQ ID NO 1
<211> LENGTH: 11
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (7)..(7)
<223> OTHER INFORMATION: Xaa can be any naturally occurring amino acid

<400> SEQUENCE: 1

Trp Gly Gln Gly Thr Asn Xaa Thr Val Ser Ser
1               5                   10

<210> SEQ ID NO 2
<211> LENGTH: 11
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (7)..(7)
<223> OTHER INFORMATION: Xaa can be any naturally occurring amino acid

<400> SEQUENCE: 2

Trp Gly Lys Gly Thr Asn Xaa Thr Val Ser Ser
1               5                   10

<210> SEQ ID NO 3
<211> LENGTH: 11
<212> TYPE: PRT
```

```
<213> ORGANISM: Artificial Sequence
<220> FEATURE:
<223> OTHER INFORMATION: NXT motif
<220> FEATURE:
<221> NAME/KEY: SITE
<222> LOCATION: (7)..(7)
<223> OTHER INFORMATION: Xaa can be any naturally occurring amino acid

<400> SEQUENCE: 3

Arg Gly Gln Gly Thr Asn Xaa Thr Val Ser Ser
 1               5                  10

<210> SEQ ID NO 4
<211> LENGTH: 11
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (7)..(7)
<223> OTHER INFORMATION: Xaa can be any naturally occurring amino acid

<400> SEQUENCE: 4

Trp Gly Leu Gly Thr Asn Xaa Thr Ile Ser Ser
 1               5                  10

<210> SEQ ID NO 5
<211> LENGTH: 11
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (7)..(7)
<223> OTHER INFORMATION: Xaa can be any naturally occurring amino acid

<400> SEQUENCE: 5

Gly Ser Gln Gly Thr Asn Xaa Thr Val Ser Ser
 1               5                  10

<210> SEQ ID NO 6
<211> LENGTH: 11
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (7)..(7)
<223> OTHER INFORMATION: Xaa can be any naturally occurring amino acid

<400> SEQUENCE: 6

Leu Arg Gly Gly Thr Asn Xaa Thr Val Ser Ser
 1               5                  10

<210> SEQ ID NO 7
<211> LENGTH: 11
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (7)..(7)
<223> OTHER INFORMATION: Xaa can be any naturally occurring amino acid

<400> SEQUENCE: 7

Arg Gly Gln Gly Thr Asn Xaa Thr Val Ser Ser
```

<210> SEQ ID NO 8
<211> LENGTH: 11
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (7)..(7)
<223> OTHER INFORMATION: Xaa can be any naturally occurring amino acid

<400> SEQUENCE: 8

Arg Ser Arg Gly Ile Asn Xaa Thr Val Ser Ser
1               5                   10

<210> SEQ ID NO 9
<211> LENGTH: 11
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (7)..(7)
<223> OTHER INFORMATION: Xaa can be any naturally occurring amino acid

<400> SEQUENCE: 9

Trp Gly Lys Gly Thr Asn Xaa Thr Val Ser Ser
1               5                   10

<210> SEQ ID NO 10
<211> LENGTH: 11
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (7)..(7)
<223> OTHER INFORMATION: Xaa can be any naturally occurring amino acid

<400> SEQUENCE: 10

Trp Gly Gln Gly Thr Asn Xaa Ser Val Ser Ser
1               5                   10

<210> SEQ ID NO 11
<211> LENGTH: 10
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (6)..(6)
<223> OTHER INFORMATION: Xaa can be any naturally occurring amino acid

<400> SEQUENCE: 11

Trp Gly Lys Gly Asn Xaa Ser Val Ser Ser
1               5                   10

<210> SEQ ID NO 12
<211> LENGTH: 11
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (7)..(7)
<223> OTHER INFORMATION: Xaa can be any naturally occurring amino acid

<400> SEQUENCE: 12

Arg Gly Gln Gly Thr Asn Xaa Ser Val Ser Ser
1               5                   10

<210> SEQ ID NO 13
<211> LENGTH: 11
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (7)..(7)
<223> OTHER INFORMATION: Xaa can be any naturally occurring amino acid

<400> SEQUENCE: 13

Trp Gly Leu Gly Thr Asn Xaa Ser Ile Ser Ser
1               5                   10

<210> SEQ ID NO 14
<211> LENGTH: 11
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (7)..(7)
<223> OTHER INFORMATION: Xaa can be any naturally occurring amino acid

<400> SEQUENCE: 14

Gly Ser Gln Gly Thr Asn Xaa Ser Val Ser Ser
1               5                   10

<210> SEQ ID NO 15
<211> LENGTH: 11
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (7)..(7)
<223> OTHER INFORMATION: Xaa can be any naturally occurring amino acid

<400> SEQUENCE: 15

Leu Arg Gly Gly Thr Asn Xaa Ser Val Ser Ser
1               5                   10

<210> SEQ ID NO 16
<211> LENGTH: 11
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (7)..(7)
<223> OTHER INFORMATION: Xaa can be any naturally occurring amino acid

<400> SEQUENCE: 16

Arg Gly Gln Gly Thr Asn Xaa Ser Val Ser Ser
1               5                   10

<210> SEQ ID NO 17
<211> LENGTH: 11

```
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (7)..(7)
<223> OTHER INFORMATION: Xaa can be any naturally occurring amino acid

<400> SEQUENCE: 17

Arg Ser Arg Gly Ile Asn Xaa Ser Val Ser Ser
1               5                   10

<210> SEQ ID NO 18
<211> LENGTH: 11
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (7)..(7)
<223> OTHER INFORMATION: Xaa can be any naturally occurring amino acid

<400> SEQUENCE: 18

Trp Gly Lys Gly Thr Asn Xaa Ser Val Ser Ser
1               5                   10

<210> SEQ ID NO 19
<211> LENGTH: 11
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (9)..(9)
<223> OTHER INFORMATION: Xaa can be any naturally occurring amino acid

<400> SEQUENCE: 19

Trp Gly Gln Gly Thr Leu Val Asn Xaa Thr Ser
1               5                   10

<210> SEQ ID NO 20
<211> LENGTH: 11
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (9)..(9)
<223> OTHER INFORMATION: Xaa can be any naturally occurring amino acid

<400> SEQUENCE: 20

Trp Gly Gln Gly Thr Gln Val Asn Xaa Thr Ser
1               5                   10

<210> SEQ ID NO 21
<211> LENGTH: 11
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (9)..(9)
<223> OTHER INFORMATION: Xaa can be any naturally occurring amino acid

<400> SEQUENCE: 21
```

Trp Gly Lys Gly Thr Leu Val Asn Xaa Thr Ser
1               5                   10

<210> SEQ ID NO 22
<211> LENGTH: 11
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (9)..(9)
<223> OTHER INFORMATION: Xaa can be any naturally occurring amino acid

<400> SEQUENCE: 22

Arg Gly Gln Gly Thr Arg Val Asn Xaa Thr Ser
1               5                   10

<210> SEQ ID NO 23
<211> LENGTH: 11
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (9)..(9)
<223> OTHER INFORMATION: Xaa can be any naturally occurring amino acid

<400> SEQUENCE: 23

Trp Gly Leu Gly Thr Gln Val Asn Xaa Thr Ser
1               5                   10

<210> SEQ ID NO 24
<211> LENGTH: 11
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (9)..(9)
<223> OTHER INFORMATION: Xaa can be any naturally occurring amino acid

<400> SEQUENCE: 24

Gly Ser Gln Gly Thr Gln Val Asn Xaa Thr Ser
1               5                   10

<210> SEQ ID NO 25
<211> LENGTH: 11
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (9)..(9)
<223> OTHER INFORMATION: Xaa can be any naturally occurring amino acid

<400> SEQUENCE: 25

Leu Arg Gly Gly Thr Gln Val Asn Xaa Thr Ser
1               5                   10

<210> SEQ ID NO 26
<211> LENGTH: 11
<212> TYPE: PRT
<213> ORGANISM: Artificial Sequence
<220> FEATURE:
<223> OTHER INFORMATION: NXT motif
<220> FEATURE:

```
<221> NAME/KEY: SITE
<222> LOCATION: (9)..(9)
<223> OTHER INFORMATION: Xaa can be any naturally occurring amino acid

<400> SEQUENCE: 26

Arg Gly Gln Gly Thr Leu Val Asn Xaa Thr Ser
1               5                   10

<210> SEQ ID NO 27
<211> LENGTH: 11
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (9)..(9)
<223> OTHER INFORMATION: Xaa can be any naturally occurring amino acid

<400> SEQUENCE: 27

Arg Ser Arg Gly Ile Gln Val Asn Xaa Thr Ser
1               5                   10

<210> SEQ ID NO 28
<211> LENGTH: 11
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (9)..(9)
<223> OTHER INFORMATION: Xaa can be any naturally occurring amino acid

<400> SEQUENCE: 28

Trp Gly Lys Gly Thr Gln Val Asn Xaa Thr Ser
1               5                   10

<210> SEQ ID NO 29
<211> LENGTH: 11
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (9)..(9)
<223> OTHER INFORMATION: Xaa can be any naturally occurring amino acid

<400> SEQUENCE: 29

Trp Gly Gln Gly Thr Leu Val Asn Xaa Ser Ser
1               5                   10

<210> SEQ ID NO 30
<211> LENGTH: 11
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (9)..(9)
<223> OTHER INFORMATION: Xaa can be any naturally occurring amino acid

<400> SEQUENCE: 30

Trp Gly Gln Gly Thr Gln Val Asn Xaa Ser Ser
1               5                   10

<210> SEQ ID NO 31
```

<211> LENGTH: 11
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (9)..(9)
<223> OTHER INFORMATION: Xaa can be any naturally occurring amino acid

<400> SEQUENCE: 31

Trp Gly Lys Gly Thr Leu Val Asn Xaa Ser Ser
1               5                   10

<210> SEQ ID NO 32
<211> LENGTH: 11
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (9)..(9)
<223> OTHER INFORMATION: Xaa can be any naturally occurring amino acid

<400> SEQUENCE: 32

Arg Gly Gln Gly Thr Arg Val Asn Xaa Ser Ser
1               5                   10

<210> SEQ ID NO 33
<211> LENGTH: 11
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (9)..(9)
<223> OTHER INFORMATION: Xaa can be any naturally occurring amino acid

<400> SEQUENCE: 33

Trp Gly Leu Gly Thr Gln Val Asn Xaa Ser Ser
1               5                   10

<210> SEQ ID NO 34
<211> LENGTH: 11
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (9)..(9)
<223> OTHER INFORMATION: Xaa can be any naturally occurring amino acid

<400> SEQUENCE: 34

Gly Ser Gln Gly Thr Gln Val Asn Xaa Ser Ser
1               5                   10

<210> SEQ ID NO 35
<211> LENGTH: 11
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (9)..(9)
<223> OTHER INFORMATION: Xaa can be any naturally occurring amino acid

<400> SEQUENCE: 35

-continued

Leu Arg Gly Gly Thr Gln Val Asn Xaa Ser Ser
1               5                  10

<210> SEQ ID NO 36
<211> LENGTH: 11
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (9)..(9)
<223> OTHER INFORMATION: Xaa can be any naturally occurring amino acid

<400> SEQUENCE: 36

Arg Gly Gln Gly Thr Leu Val Asn Xaa Ser Ser
1               5                  10

<210> SEQ ID NO 37
<211> LENGTH: 11
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (9)..(9)
<223> OTHER INFORMATION: Xaa can be any naturally occurring amino acid

<400> SEQUENCE: 37

Arg Ser Arg Gly Ile Gln Val Asn Xaa Ser Ser
1               5                  10

<210> SEQ ID NO 38
<211> LENGTH: 11
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (9)..(9)
<223> OTHER INFORMATION: Xaa can be any naturally occurring amino acid

<400> SEQUENCE: 38

Arg Ser Arg Gly Ile Gln Val Asn Xaa Ser Ser
1               5                  10

<210> SEQ ID NO 39
<211> LENGTH: 12
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (11)..(11)
<223> OTHER INFORMATION: Xaa can be any naturally occurring amino acid

<400> SEQUENCE: 39

Trp Gly Gln Gly Thr Leu Val Thr Val Asn Xaa Thr
1               5                  10

<210> SEQ ID NO 40
<211> LENGTH: 12
<212> TYPE: PRT
<213> ORGANISM: Artificial Sequence
<220> FEATURE:
<223> OTHER INFORMATION: NXT motif

```
<220> FEATURE:
<221> NAME/KEY: SITE
<222> LOCATION: (11)..(11)
<223> OTHER INFORMATION: Xaa can be any naturally occurring amino acid

<400> SEQUENCE: 40

Trp Gly Gln Gly Thr Gln Val Thr Val Asn Xaa Thr
1               5                   10

<210> SEQ ID NO 41
<211> LENGTH: 12
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (11)..(11)
<223> OTHER INFORMATION: Xaa can be any naturally occurring amino acid

<400> SEQUENCE: 41

Trp Gly Lys Gly Thr Leu Val Thr Val Asn Xaa Thr
1               5                   10

<210> SEQ ID NO 42
<211> LENGTH: 12
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (11)..(11)
<223> OTHER INFORMATION: Xaa can be any naturally occurring amino acid

<400> SEQUENCE: 42

Arg Gly Gln Gly Thr Arg Val Thr Val Asn Xaa Thr
1               5                   10

<210> SEQ ID NO 43
<211> LENGTH: 12
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (11)..(11)
<223> OTHER INFORMATION: Xaa can be any naturally occurring amino acid

<400> SEQUENCE: 43

Trp Gly Leu Gly Thr Gln Val Thr Ile Asn Xaa Thr
1               5                   10

<210> SEQ ID NO 44
<211> LENGTH: 12
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (11)..(11)
<223> OTHER INFORMATION: Xaa can be any naturally occurring amino acid

<400> SEQUENCE: 44

Gly Ser Gln Gly Thr Gln Val Thr Val Asn Xaa Thr
1               5                   10
```

```
<210> SEQ ID NO 45
<211> LENGTH: 12
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (11)..(11)
<223> OTHER INFORMATION: Xaa can be any naturally occurring amino acid

<400> SEQUENCE: 45

Leu Arg Gly Gly Thr Gln Val Thr Val Asn Xaa Thr
1               5                   10

<210> SEQ ID NO 46
<211> LENGTH: 12
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (11)..(11)
<223> OTHER INFORMATION: Xaa can be any naturally occurring amino acid

<400> SEQUENCE: 46

Arg Gly Gln Gly Thr Leu Val Thr Val Asn Xaa Thr
1               5                   10

<210> SEQ ID NO 47
<211> LENGTH: 12
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (11)..(11)
<223> OTHER INFORMATION: Xaa can be any naturally occurring amino acid

<400> SEQUENCE: 47

Arg Ser Arg Gly Ile Gln Val Thr Val Asn Xaa Thr
1               5                   10

<210> SEQ ID NO 48
<211> LENGTH: 12
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (11)..(11)
<223> OTHER INFORMATION: Xaa can be any naturally occurring amino acid

<400> SEQUENCE: 48

Trp Gly Lys Gly Thr Gln Val Thr Val Asn Xaa Thr
1               5                   10

<210> SEQ ID NO 49
<211> LENGTH: 12
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (11)..(11)
<223> OTHER INFORMATION: Xaa can be any naturally occurring amino acid
```

```
<400> SEQUENCE: 49

Trp Gly Gln Gly Thr Leu Val Thr Val Asn Xaa Ser
1               5                   10

<210> SEQ ID NO 50
<211> LENGTH: 12
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (11)..(11)
<223> OTHER INFORMATION: Xaa can be any naturally occurring amino acid

<400> SEQUENCE: 50

Trp Gly Gln Gly Thr Gln Val Thr Val Asn Xaa Ser
1               5                   10

<210> SEQ ID NO 51
<211> LENGTH: 12
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (11)..(11)
<223> OTHER INFORMATION: Xaa can be any naturally occurring amino acid

<400> SEQUENCE: 51

Trp Gly Lys Gly Thr Leu Val Thr Val Asn Xaa Ser
1               5                   10

<210> SEQ ID NO 52
<211> LENGTH: 12
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (11)..(11)
<223> OTHER INFORMATION: Xaa can be any naturally occurring amino acid

<400> SEQUENCE: 52

Arg Gly Gln Gly Thr Arg Val Thr Val Asn Xaa Ser
1               5                   10

<210> SEQ ID NO 53
<211> LENGTH: 12
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (11)..(11)
<223> OTHER INFORMATION: Xaa can be any naturally occurring amino acid

<400> SEQUENCE: 53

Trp Gly Leu Gly Thr Gln Val Thr Ile Asn Xaa Ser
1               5                   10

<210> SEQ ID NO 54
<211> LENGTH: 12
<212> TYPE: PRT
<213> ORGANISM: Artificial Sequence
<220> FEATURE:
```

```
<223> OTHER INFORMATION: NXS motif
<220> FEATURE:
<221> NAME/KEY: SITE
<222> LOCATION: (11)..(11)
<223> OTHER INFORMATION: Xaa can be any naturally occurring amino acid

<400> SEQUENCE: 54

Gly Ser Gln Gly Thr Gln Val Thr Val Asn Xaa Ser
1               5                   10

<210> SEQ ID NO 55
<211> LENGTH: 12
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (11)..(11)
<223> OTHER INFORMATION: Xaa can be any naturally occurring amino acid

<400> SEQUENCE: 55

Leu Arg Gly Gly Thr Gln Val Thr Val Asn Xaa Ser
1               5                   10

<210> SEQ ID NO 56
<211> LENGTH: 12
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (11)..(11)
<223> OTHER INFORMATION: Xaa can be any naturally occurring amino acid

<400> SEQUENCE: 56

Arg Gly Gln Gly Thr Leu Val Thr Val Asn Xaa Ser
1               5                   10

<210> SEQ ID NO 57
<211> LENGTH: 12
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (11)..(11)
<223> OTHER INFORMATION: Xaa can be any naturally occurring amino acid

<400> SEQUENCE: 57

Arg Ser Arg Gly Ile Gln Val Thr Val Asn Xaa Ser
1               5                   10

<210> SEQ ID NO 58
<211> LENGTH: 12
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (11)..(11)
<223> OTHER INFORMATION: Xaa can be any naturally occurring amino acid

<400> SEQUENCE: 58

Trp Gly Lys Gly Thr Gln Val Thr Val Asn Xaa Ser
1               5                   10
```

```
<210> SEQ ID NO 59
<211> LENGTH: 13
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (12)..(12)
<223> OTHER INFORMATION: Xaa can be any naturally occurring amino acid

<400> SEQUENCE: 59

Trp Gly Gln Gly Thr Leu Val Thr Val Ser Asn Xaa Thr
1               5                   10

<210> SEQ ID NO 60
<211> LENGTH: 13
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (12)..(12)
<223> OTHER INFORMATION: Xaa can be any naturally occurring amino acid

<400> SEQUENCE: 60

Trp Gly Gln Gly Thr Gln Val Thr Val Ser Asn Xaa Thr
1               5                   10

<210> SEQ ID NO 61
<211> LENGTH: 13
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (12)..(12)
<223> OTHER INFORMATION: Xaa can be any naturally occurring amino acid

<400> SEQUENCE: 61

Trp Gly Lys Gly Thr Leu Val Thr Val Ser Asn Xaa Thr
1               5                   10

<210> SEQ ID NO 62
<211> LENGTH: 13
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (12)..(12)
<223> OTHER INFORMATION: Xaa can be any naturally occurring amino acid

<400> SEQUENCE: 62

Arg Gly Gln Gly Thr Arg Val Thr Val Ser Asn Xaa Thr
1               5                   10

<210> SEQ ID NO 63
<211> LENGTH: 13
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (12)..(12)
<223> OTHER INFORMATION: Xaa can be any naturally occurring amino acid
```

<400> SEQUENCE: 63

Trp Gly Leu Gly Thr Gln Val Thr Ile Ser Asn Xaa Thr
1               5                   10

<210> SEQ ID NO 64
<211> LENGTH: 13
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (12)..(12)
<223> OTHER INFORMATION: Xaa can be any naturally occurring amino acid

<400> SEQUENCE: 64

Gly Ser Gln Gly Thr Gln Val Thr Val Ser Asn Xaa Thr
1               5                   10

<210> SEQ ID NO 65
<211> LENGTH: 13
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (12)..(12)
<223> OTHER INFORMATION: Xaa can be any naturally occurring amino acid

<400> SEQUENCE: 65

Leu Arg Gly Gly Thr Gln Val Thr Val Ser Asn Xaa Thr
1               5                   10

<210> SEQ ID NO 66
<211> LENGTH: 13
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (12)..(12)
<223> OTHER INFORMATION: Xaa can be any naturally occurring amino acid

<400> SEQUENCE: 66

Arg Gly Gln Gly Thr Leu Val Thr Val Ser Asn Xaa Thr
1               5                   10

<210> SEQ ID NO 67
<211> LENGTH: 13
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (12)..(12)
<223> OTHER INFORMATION: Xaa can be any naturally occurring amino acid

<400> SEQUENCE: 67

Arg Ser Arg Gly Ile Gln Val Thr Val Ser Asn Xaa Thr
1               5                   10

<210> SEQ ID NO 68
<211> LENGTH: 13
<212> TYPE: PRT
<213> ORGANISM: Artificial Sequence

```
<220> FEATURE:
<223> OTHER INFORMATION: NXT motif
<220> FEATURE:
<221> NAME/KEY: SITE
<222> LOCATION: (12)..(12)
<223> OTHER INFORMATION: Xaa can be any naturally occurring amino acid

<400> SEQUENCE: 68

Trp Gly Lys Gly Thr Gln Val Thr Val Ser Asn Xaa Thr
1               5                   10

<210> SEQ ID NO 69
<211> LENGTH: 13
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (12)..(12)
<223> OTHER INFORMATION: Xaa can be any naturally occurring amino acid

<400> SEQUENCE: 69

Trp Gly Gln Gly Thr Leu Val Thr Val Ser Asn Xaa Ser
1               5                   10

<210> SEQ ID NO 70
<211> LENGTH: 13
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (12)..(12)
<223> OTHER INFORMATION: Xaa can be any naturally occurring amino acid

<400> SEQUENCE: 70

Trp Gly Gln Gly Thr Gln Val Thr Val Ser Asn Xaa Ser
1               5                   10

<210> SEQ ID NO 71
<211> LENGTH: 13
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (12)..(12)
<223> OTHER INFORMATION: Xaa can be any naturally occurring amino acid

<400> SEQUENCE: 71

Trp Gly Lys Gly Thr Leu Val Thr Val Ser Asn Xaa Ser
1               5                   10

<210> SEQ ID NO 72
<211> LENGTH: 13
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (12)..(12)
<223> OTHER INFORMATION: Xaa can be any naturally occurring amino acid

<400> SEQUENCE: 72

Arg Gly Gln Gly Thr Arg Val Thr Val Ser Asn Xaa Ser
1               5                   10
```

<210> SEQ ID NO 73
<211> LENGTH: 13
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (12)..(12)
<223> OTHER INFORMATION: Xaa can be any naturally occurring amino acid

<400> SEQUENCE: 73

Trp Gly Leu Gly Thr Gln Val Thr Ile Ser Asn Xaa Ser
1               5                   10

<210> SEQ ID NO 74
<211> LENGTH: 13
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (12)..(12)
<223> OTHER INFORMATION: Xaa can be any naturally occurring amino acid

<400> SEQUENCE: 74

Gly Ser Gln Gly Thr Gln Val Thr Val Ser Asn Xaa Ser
1               5                   10

<210> SEQ ID NO 75
<211> LENGTH: 13
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (12)..(12)
<223> OTHER INFORMATION: Xaa can be any naturally occurring amino acid

<400> SEQUENCE: 75

Leu Arg Gly Gly Thr Gln Val Thr Val Ser Asn Xaa Ser
1               5                   10

<210> SEQ ID NO 76
<211> LENGTH: 13
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (12)..(12)
<223> OTHER INFORMATION: Xaa can be any naturally occurring amino acid

<400> SEQUENCE: 76

Arg Gly Gln Gly Thr Leu Val Thr Val Ser Asn Xaa Ser
1               5                   10

<210> SEQ ID NO 77
<211> LENGTH: 13
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (12)..(12)

<223> OTHER INFORMATION: Xaa can be any naturally occurring amino acid

<400> SEQUENCE: 77

Arg Ser Arg Gly Ile Gln Val Thr Val Ser Asn Xaa Ser
1               5                   10

<210> SEQ ID NO 78
<211> LENGTH: 13
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (12)..(12)
<223> OTHER INFORMATION: Xaa can be any naturally occurring amino acid

<400> SEQUENCE: 78

Trp Gly Lys Gly Thr Gln Val Thr Val Ser Asn Xaa Ser
1               5                   10

<210> SEQ ID NO 79
<211> LENGTH: 14
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (13)..(13)
<223> OTHER INFORMATION: Xaa can be any naturally occurring amino acid

<400> SEQUENCE: 79

Trp Gly Gln Gly Thr Leu Val Thr Val Ser Ser Asn Xaa Thr
1               5                   10

<210> SEQ ID NO 80
<211> LENGTH: 14
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (13)..(13)
<223> OTHER INFORMATION: Xaa can be any naturally occurring amino acid

<400> SEQUENCE: 80

Trp Gly Gln Gly Thr Gln Val Thr Val Ser Ser Asn Xaa Thr
1               5                   10

<210> SEQ ID NO 81
<211> LENGTH: 14
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (13)..(13)
<223> OTHER INFORMATION: Xaa can be any naturally occurring amino acid

<400> SEQUENCE: 81

Trp Gly Lys Gly Thr Leu Val Thr Val Ser Ser Asn Xaa Thr
1               5                   10

<210> SEQ ID NO 82
<211> LENGTH: 14
<212> TYPE: PRT

```
<213> ORGANISM: Artificial Sequence
<220> FEATURE:
<223> OTHER INFORMATION: NXT motif
<220> FEATURE:
<221> NAME/KEY: SITE
<222> LOCATION: (13)..(13)
<223> OTHER INFORMATION: Xaa can be any naturally occurring amino acid

<400> SEQUENCE: 82

Arg Gly Gln Gly Thr Arg Val Thr Val Ser Ser Asn Xaa Thr
1               5                   10

<210> SEQ ID NO 83
<211> LENGTH: 14
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (13)..(13)
<223> OTHER INFORMATION: Xaa can be any naturally occurring amino acid

<400> SEQUENCE: 83

Trp Gly Leu Gly Thr Gln Val Thr Ile Ser Ser Asn Xaa Thr
1               5                   10

<210> SEQ ID NO 84
<211> LENGTH: 14
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (13)..(13)
<223> OTHER INFORMATION: Xaa can be any naturally occurring amino acid

<400> SEQUENCE: 84

Gly Ser Gln Gly Thr Gln Val Thr Val Ser Ser Asn Xaa Thr
1               5                   10

<210> SEQ ID NO 85
<211> LENGTH: 14
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (13)..(13)
<223> OTHER INFORMATION: Xaa can be any naturally occurring amino acid

<400> SEQUENCE: 85

Leu Arg Gly Gly Thr Gln Val Thr Val Ser Ser Asn Xaa Thr
1               5                   10

<210> SEQ ID NO 86
<211> LENGTH: 14
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (13)..(13)
<223> OTHER INFORMATION: Xaa can be any naturally occurring amino acid

<400> SEQUENCE: 86

Arg Gly Gln Gly Thr Leu Val Thr Val Ser Ser Asn Xaa Thr
```

<210> SEQ ID NO 87
<211> LENGTH: 14
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (13)..(13)
<223> OTHER INFORMATION: Xaa can be any naturally occurring amino acid

<400> SEQUENCE: 87

Arg Ser Arg Gly Ile Gln Val Thr Val Ser Ser Asn Xaa Thr
1               5                   10

<210> SEQ ID NO 88
<211> LENGTH: 14
<212> TYPE: PRT
<213> ORGANISM: Artificial Sequence
<220> FEATURE:
<223> OTHER INFORMATION: NXT motif
<220> FEATURE:
<221> NAME/KEY: SITE
<222> LOCATION: (13)..(13)
<223> OTHER INFORMATION: Xaa can be any naturally occurring amino acid

<400> SEQUENCE: 88

Trp Gly Lys Gly Thr Gln Val Thr Val Ser Ser Asn Xaa Thr
1               5                   10

<210> SEQ ID NO 89
<211> LENGTH: 14
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (13)..(13)
<223> OTHER INFORMATION: Xaa can be any naturally occurring amino acid

<400> SEQUENCE: 89

Trp Gly Gln Gly Thr Leu Val Thr Val Ser Ser Asn Xaa Ser
1               5                   10

<210> SEQ ID NO 90
<211> LENGTH: 14
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (13)..(13)
<223> OTHER INFORMATION: Xaa can be any naturally occurring amino acid

<400> SEQUENCE: 90

Trp Gly Gln Gly Thr Gln Val Thr Val Ser Ser Asn Xaa Ser
1               5                   10

<210> SEQ ID NO 91
<211> LENGTH: 14
<212> TYPE: PRT
<213> ORGANISM: Artificial Sequence
<220> FEATURE:
<223> OTHER INFORMATION: NXS motif
<220> FEATURE:
<221> NAME/KEY: SITE

```
<222> LOCATION: (13)..(13)
<223> OTHER INFORMATION: Xaa can be any naturally occurring amino acid

<400> SEQUENCE: 91

Trp Gly Lys Gly Thr Leu Val Thr Val Ser Ser Asn Xaa Ser
1               5                   10

<210> SEQ ID NO 92
<211> LENGTH: 14
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (13)..(13)
<223> OTHER INFORMATION: Xaa can be any naturally occurring amino acid

<400> SEQUENCE: 92

Arg Gly Gln Gly Thr Arg Val Thr Val Ser Ser Asn Xaa Ser
1               5                   10

<210> SEQ ID NO 93
<211> LENGTH: 14
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (13)..(13)
<223> OTHER INFORMATION: Xaa can be any naturally occurring amino acid

<400> SEQUENCE: 93

Trp Gly Leu Gly Thr Gln Val Thr Ile Ser Ser Asn Xaa Ser
1               5                   10

<210> SEQ ID NO 94
<211> LENGTH: 14
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (13)..(13)
<223> OTHER INFORMATION: Xaa can be any naturally occurring amino acid

<400> SEQUENCE: 94

Gly Ser Gln Gly Thr Gln Val Thr Val Ser Ser Asn Xaa Ser
1               5                   10

<210> SEQ ID NO 95
<211> LENGTH: 14
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (13)..(13)
<223> OTHER INFORMATION: Xaa can be any naturally occurring amino acid

<400> SEQUENCE: 95

Leu Arg Gly Gly Thr Gln Val Thr Val Ser Ser Asn Xaa Ser
1               5                   10

<210> SEQ ID NO 96
<211> LENGTH: 14
```

```
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (13)..(13)
<223> OTHER INFORMATION: Xaa can be any naturally occurring amino acid

<400> SEQUENCE: 96

Arg Gly Gln Gly Thr Leu Val Thr Val Ser Ser Asn Xaa Ser
1               5                   10

<210> SEQ ID NO 97
<211> LENGTH: 14
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (13)..(13)
<223> OTHER INFORMATION: Xaa can be any naturally occurring amino acid

<400> SEQUENCE: 97

Arg Ser Arg Gly Ile Gln Val Thr Val Ser Ser Asn Xaa Ser
1               5                   10

<210> SEQ ID NO 98
<211> LENGTH: 14
<212> TYPE: PRT
<213> ORGANISM: Artificial Sequence
<220> FEATURE:
<223> OTHER INFORMATION: NXS motif
<220> FEATURE:
<221> NAME/KEY: SITE
<222> LOCATION: (13)..(13)
<223> OTHER INFORMATION: Xaa can be any naturally occurring amino acid

<400> SEQUENCE: 98

Trp Gly Lys Gly Thr Gln Val Thr Val Ser Ser Asn Xaa Ser
1               5                   10

<210> SEQ ID NO 99
<211> LENGTH: 121
<212> TYPE: PRT
<213> ORGANISM: Artificial Sequence
<220> FEATURE:
<223> OTHER INFORMATION: ISVD sequence

<400> SEQUENCE: 99

His His His His His His Glu Val Gln Leu Val Glu Ser Gly Gly Gly
1               5                   10                  15

Leu Val Gln Pro Gly Asn Ser Leu Arg Leu Ser Cys Ala Ala Ser Gly
            20                  25                  30

Phe Thr Phe Ser Ser Phe Gly Met Ser Trp Val Arg Gln Ala Pro Gly
        35                  40                  45

Lys Gly Leu Glu Trp Val Ser Ser Ile Ser Gly Ser Gly Ser Asp Thr
    50                  55                  60

Leu Tyr Ala Asp Ser Val Lys Gly Arg Phe Thr Ile Ser Arg Asp Asn
65                  70                  75                  80

Ala Lys Thr Thr Leu Tyr Leu Gln Met Asn Ser Leu Arg Pro Glu Asp
                85                  90                  95

Thr Ala Val Tyr Tyr Cys Thr Ile Gly Gly Ser Leu Ser Arg Ser Ser
            100                 105                 110
```

Gln Gly Thr Leu Val Thr Val Ser Ser
        115                 120

<210> SEQ ID NO 100
<211> LENGTH: 121
<212> TYPE: PRT
<213> ORGANISM: Artificial Sequence
<220> FEATURE:
<223> OTHER INFORMATION: ISVD sequence

<400> SEQUENCE: 100

His His His His His His Glu Val Gln Leu Val Glu Ser Gly Gly Gly
1               5                   10                  15

Leu Val Gln Pro Gly Asn Ser Leu Arg Leu Ser Cys Ala Ala Ser Gly
            20                  25                  30

Phe Thr Phe Ser Ser Phe Gly Met Ser Trp Val Arg Gln Ala Pro Gly
        35                  40                  45

Lys Gly Leu Glu Trp Val Ser Ser Ile Ser Gly Ser Gly Ser Asp Thr
    50                  55                  60

Leu Tyr Ala Asp Ser Val Lys Gly Arg Phe Thr Ile Ser Arg Asp Asn
65                  70                  75                  80

Ala Lys Thr Thr Leu Tyr Leu Gln Met Asn Ser Leu Arg Pro Glu Asp
                85                  90                  95

Thr Ala Val Tyr Tyr Cys Thr Ile Gly Gly Ser Leu Ser Arg Ser Ser
            100                 105                 110

Gln Gly Thr Asn Val Thr Val Ser Ser
        115                 120

<210> SEQ ID NO 101
<211> LENGTH: 121
<212> TYPE: PRT
<213> ORGANISM: Artificial Sequence
<220> FEATURE:
<223> OTHER INFORMATION: ISVD sequence

<400> SEQUENCE: 101

His His His His His His Glu Val Gln Leu Val Glu Ser Gly Gly Gly
1               5                   10                  15

Leu Val Gln Pro Gly Asn Ser Leu Arg Leu Ser Cys Ala Ala Ser Gly
            20                  25                  30

Phe Thr Phe Ser Ser Phe Gly Met Ser Trp Val Arg Gln Ala Pro Gly
        35                  40                  45

Lys Gly Leu Glu Trp Val Ser Ser Ile Ser Gly Ser Gly Ser Asp Thr
    50                  55                  60

Leu Tyr Ala Asp Ser Val Lys Gly Arg Phe Thr Ile Ser Arg Asp Asn
65                  70                  75                  80

Ala Lys Thr Thr Leu Tyr Leu Gln Met Asn Ser Leu Arg Pro Asn Asp
                85                  90                  95

Thr Ala Val Tyr Tyr Cys Thr Ile Gly Gly Ser Leu Ser Arg Ser Ser
            100                 105                 110

Gln Gly Thr Leu Val Thr Val Ser Ser
        115                 120

<210> SEQ ID NO 102
<211> LENGTH: 5
<212> TYPE: PRT
<213> ORGANISM: Artificial Sequence
<220> FEATURE:
<223> OTHER INFORMATION: C-terminal sequence

```
<400> SEQUENCE: 102

Val Thr Val Ser Ser
1               5
```

GLYCOSYLATED IMMUNOGLOBULIN SINGLE VARIABLE DOMAINS

RELATED APPLICATIONS

This application is a national stage filing under 35 U.S.C. § 371 of International Application No. PCT/EP2016/055947, filed Mar. 18, 2016, and claims the benefit under 35 U.S.C. § 119(e) of U.S. provisional application Ser. No. 62/135,968, filed Mar. 20, 2015, the entire contents of each of which is incorporated by reference herein in its entirety.

The present invention relates to glycosylated immunoglobulin variable domains, and in particular to glycosylated immunoglobulin single variable domains (the latter also being referred to herein by means of the abbreviation "ISV" or "ISVD").

The present invention relates to glycosylated immunoglobulin heavy-chain variable domains (also referred to herein as "VH domains"), and in particular to glycosylated immunoglobulin heavy-chain ISVD's.

The invention in particular relates to immunoglobulin (single) variable domains that are glycosylated in such a way (i.e. as further described herein, and also referred to herein as "glycosylation of the invention") that the binding of said immunoglobulin (single) variable domains by so-called "pre-existing antibodies" (as further described herein and in the prior art cited herein) is prevented and/or reduced (i.e. partially or essentially completely) compared to the same immunoglobulin (single) variable domain without the glycosylation of the invention being present (said comparison being as further described herein).

The invention also relates to immunoglobulin (single) variable domains that contain within their sequence a glycosylation site that is as further described herein (also referred to herein as a "glycosylation site of the invention"). VH domains that contain a glycosylation site of the invention are also referred to herein as "VH domains of the invention". Similarly, ISVs/ISVDs that contain a glycosylation site of the invention are also referred to herein as "ISVs/ISVDs of the invention"

The immunoglobulin (single) variable domains of the invention can be in glycosylated form (in which case they are referred to herein as "glycosylated") or in non-glycosylated from (in which case they are referred to herein as "non-glycosylated"). When they are in non-glycosylated form, they can be converted into the corresponding glycosylated form by glycosylating the glycosylation site of the invention that is present in their sequence. Alternatively, the glycosylated immunoglobulin single variable domains of the invention can be obtained by suitably expressing a nucleotide sequence that encodes the non-glycosylated form in a host cell or host organism that will glycosylate the expressed sequence as part of its post-translational modification(s) of expressed protein sequences.

The invention also relates to polypeptides, proteins and other compounds, constructs or chemical entities that contain or comprise at least one immunoglobulin (single) variable domain according to the invention (such polypeptides, proteins, compounds, constructs and chemical entities are also referred to herein as "compounds of the invention"). Again, such compounds of the invention can generally be in glycosylated form (meaning that the one or more immunoglobulin (single) variable domains of the invention present in the compound of the invention are in glycosylated form) or in non-glycosylated form (meaning that the one or more immunoglobulin (single) variable domains of the invention present in the compound of the invention are in non-glycosylated form); and when the compound of the invention is in non-glycosylated form, it can be converted into its corresponding glycosylated form by glycosylating the glycosylation site(s) of the invention that is/are present in its sequence (i.e. in the non-glycosylated immunoglobulin (single) variable domains of the invention). Alternatively, when the compound of the invention is a protein or polypeptide (or another compound that can be obtained by expressing a nucleotide sequence encoding the same in a suitable host cell or host organism), the glycosylated compound of the invention can be obtained by suitably expressing a nucleotide sequence that encodes the non-glycosylated form of the compound in a host cell or host organism that will glycosylate the expressed sequence as part of its post-translational modification(s) of expressed protein sequences.

Usually, the immunoglobulin (single) variable domains of the invention that are present in a compound of the invention will essentially all be either glycosylated or non-glycosylated (however the invention in its broadest sense is not limited thereto).

As will become clear from the further description herein, in one particular but non-limiting aspect, the invention is applied to immunoglobulin variable domains (and in particular VH domains) that either have an exposed C-terminal region or end (as described herein; see also WO 12/175741) or that are used in (or intended for use in) applications where they have an exposed C-terminal region or end (again, as further described herein). Some preferred but non-limiting examples of the former are immunoglobulin single variable domains (also referred to herein as "ISV's" or "ISVD's") such as NANOBODIES® (including VHH's, humanized VHH's and camelized VH's such as camelized human VH's), (single domain) antibodies that are VH domains or derived from VH domains, and dAb's that are VH domains or derived from VH domains. Some preferred but non-limiting examples of the latter are VH domains that are used in (or intended for use in) single chain Fv's (ScFv's) or diabodies; as well as polypeptides, proteins, compounds, constructs and chemical entities in which an ISV forms the C-terminal end of the molecule. However, the application in its broadest sense is not limited thereto and can for example also be applied to ISV's that are part of a larger polypeptide, protein, compound, construct or other chemical entity in which the ISV does not form the C-terminal part.

Herein, the invention will be described with particular reference to VH domains, and with more particular reference to VH domains that are ISVD's or suitable for use as ISVD's (as further described herein), as these form a particularly preferred aspect of the invention. However, based on the disclosure herein (if necessary taken together with the disclosure of the prior art cited herein), the skilled person will also be able to apply the invention to immunoglobulin variable domains that are present in other formats such as ScFv's and diabodies.

Also, based on the disclosure herein, it will be clear to the skilled person that the glycosylation of the invention can also be applied analogously to light-chain domains (and in particular VL domains that are ISVD's or intended/suitable for use as ISVD's) when the same have an exposed C-terminal end that is susceptible to binding by any pre-existing antibodies or factors that might occur in the circulation of a human subject. For example, based on the disclosure herein, the skilled person will be able to introduce a suitable glycosylation site in the C-terminal region of the VL domain (preferably such that the asparagine residue of the NXT or NXS motif is at a surface-exposed position of the VL domain) and provide said site with suitable glycosylation.

The invention also relates to nucleotide sequences and nucleic acids that encode an immunoglobulin (single) variable domain or a compound of the invention (i.e. in their non-glycosylated form). Such nucleotide sequences and nucleic acids can be as further described herein, and are also referred to herein as "nucleic acid of the invention".

The invention also relates to methods for generating, expressing, producing and/or manufacturing an immunoglobulin (single) variable domain or compound of the invention (in either glycosylated or non-glycosylated form) or a nucleotide sequence of the invention (also referred to herein as "methods of the invention"). For example, in one aspect, such method of the invention (at least) includes the step of suitably introducing one or more codons that encode a glycosylation site of the invention into a nucleotide sequence or nucleic acid that encodes an immunoglobulin (single) variable domain, so as to provide a nucleic acid of the invention that encodes an immunoglobulin (single) variable domain that corresponds to the starting immunoglobulin (single) variable domain, but with a glycosylation site of the invention included within its sequence. Such a nucleic acid can then optionally be suitably expressed in a suitable host cell or host organism to provide said immunoglobulin (single) variable domain or compound of the invention in either glycosylated or non-glycosylated form (depending on the host cell or host organism used). Similarly, when the methods of the invention are to be used to provide compounds of the invention, the methods of the invention can (at least) include the step of suitably introducing one or more codons that encode a glycosylation site of the invention into those part(s) of the overall nucleotide sequences that encode the one or more immunoglobulin (single) variable domains to be present in said compound (so as to provide a nucleic acid sequence of the invention that encodes the desired compound of the invention), that can then again optionally be suitably expressed in a suitable host cell or host organism.

In one specific aspect, the methods of the invention (at least) include the step of suitably expressing a nucleic acid of the invention in a host cell or host organism that is capable of glycosylating at least one of the glycosylation sites of the invention that is encoded by/within said nucleic acid, in particular such that at least one of said glycosylation sites of the invention are glycosylated. Thus, this aspect of the methods of the invention provides a glycosylated form of the immunoglobulin (single) variable domain or compound to the invention that is encoded (in its non-glycosylated form) by the expressed nucleic acid of the invention.

The invention further relates to methods for preventing or reducing the binding of pre-existing antibodies to immunoglobulin (single) variable domains (or to polypeptides, proteins, compounds, constructs or other chemical entities comprising the same), by suitably introducing at least one glycosylation site of the invention into the same (i.e. using the methods described herein) such that in the resulting immunoglobulin (single) variable domain, polypeptide, protein, compound, construct or other chemical entity, said at least one glycosylation site of the invention is glycosylated.

The invention also relates to compositions that comprise at least one immunoglobulin (single) variable domain or compound of the invention. Such compositions may in particular be pharmaceutical compositions (i.e. suitable for administration to a human being) and may then optionally contain one or more pharmaceutically acceptable adjuvants, excipient or carrier.

These and other aspects, embodiments, applications, uses of the invention (and their associated advantages) will become clear from the further description herein.

In the present application, the amino acid residues/positions in an immunoglobulin heavy-chain variable domain will be indicated with the numbering according to Kabat. For the sake of convenience and reference, FIG. 1 gives a table listing some of the amino acid positions that will be specifically referred to herein and their numbering according to some alternative numbering systems (such as Aho and IMGT. Note: for the present description and claims, Kabat numbering is decisive; other numbering systems are given for reference only); and FIG. 2 provides a table that shows the amino acid residues that most frequently occur at each of the positions 103-113 in human VH3 domains as well as some of the main amino acid residues that can occur at the same positions in Camelid VHH domains.

Also, in the invention, an immunoglobulin variable domain is said to have "an exposed C-terminal end or region" when it is not associated with or linked to a constant domain (such as a $C_H1$ domain). Reference is made to the relevant prior art cited herein.

In particular, as described in WO 12/175741, the C-terminal region (as this term is also used herein) is part of a putative epitope on the ISV that also includes, among other residues, the amino acid residue at position 14 (and the amino acid residues next/close to the same in the amino acid sequence, such as positions 11, 13 and 15) and may also comprise the amino acid residue at position 83 (and the amino acid residues next/close to the same in the amino acid sequence, such as positions 82, 82a, 82b and 84) and/or the amino acid residue at position 108 (and the amino acid residues next/close to the same in the amino acid sequence, such as positions 107. As in WO 12/17574, this putative epitope is also collectively referred to herein as the "C-terminal region", it being understood that this C-terminal region at least comprises the C terminal sequence VTVSS (SEQ ID NO: 102) (i.e. each of positions 109, 110, 111, 112 and 113) and the amino acid residue at position 14, and may also comprise the amino acid residues at positions 83 and 108, and possibly also the amino acid residues at positions 13, 15, 82b, 83, 84 and 107.

As a result of research into single chain Fv's or "ScFv's" (which are constructs that contain immunoglobulin variable domains that, similar to ISVD's, are not associated with constant domains), it has been described in the art that the C-terminus of an immunoglobulin variable domain contains a hydrophobic patch that in a conventional full-sized antibody is buried in the interface between the variable domain and the constant domain but that becomes solvent-exposed when the variable domain is not associated with a constant domain (see for example Nieba et al., Protein Engineering, 10, 435-444 (1997) and Harmsen et al., Molecular Immunology (2000), 579-590).

It is also well known that epitopes that are usually buried within the structure of a protein (also referred to as "neo-epitopes" or "cryptic epitopes") may trigger the immune system once they become solvent-exposed, for example due to degradation, misfolding or aggregation of the protein involved. For example, in the case of buried hydrophobic portions of biomolecules (so-called "hyppos"), it has been suggested that these form part of a general damage-associated molecular pattern that leads to innate immune responses once the hyppos become solvent-exposed (see for example Seong and Matzinger, Nature Reviews 2004, 469), and various examples of previously-buried hydrophobic patches triggering immune responses have been described in the art (see for example David et al., JBC, 2001, 6370-6377; Matsuura et al., International Immunology, 2000, 1183-1192; Rasheed et al., Life Sciences 79 (2000), 2320-2328).

More generally, it is also known in the art that hydrophobic amino acids are prone to be part of B-cell epitopes (see for example WO 11/075861, page 10; and Kolaskar, FEBS 276, 172-174 (1990)). Similarly, it has been described that the hydrophobic patch at the C-terminus of a heavy-chain variable domain (as described by Nieba et al. and Harmsen et al., supra) may form B-cell epitopes which can give rise to and/or interact with (emerging and/or pre-existing) anti-drug antibodies (WO 11/075861). For this reason, it has been proposed to make mutations to some of the amino acid residues that form part of the C-terminus of the variable domains to reduce hydrophobicity and/or to remove B-cell epitopes. For example, Nieba et al. suggest to mutate positions 11, 14, 41, 84, 87 and/or 89 of a VH region (numbering according to Kabat), whereas in WO 11/075861 it is suggested to mutate positions 99, 101 and/or 148 (AHo numbering) of a VL domain or positions 12, 97, 98, 99, 103 and/or 144 of a VH domain (again AHo numbering—these positions correspond to positions 11, 83, 84, 85, 89 and 103 according to Kabat). Similarly, Harmsen et al. suggest to mutate positions 12 and 101 (IMGT numbering; these are positions 11 and 89 according to Kabat) to compensate for the absence of a $C_H1$ domain; and they also identify a specific subfamily of VHH's (called "VHH4's") that contain amino acids that are suitable candidates for substitutions at these positions.

It has also been described in the art (see for example WO 12/175741 and the references cited in the next paragraphs) that biological samples obtained from human subjects may contain (pre-existing) proteins or factors that are capable of binding to the exposed C-terminal region or end of an immunoglobulin variable domain (for example, the C-terminal region or end of an ISVD or of a VH or VL domain in an ScFv or diabody).

For example, WO 2013/024059 states on page 2, lines 20-24 that "in sera from some healthy naïve human subjects, pre-existing anti-VH autoantibodies are present that can bind both VH domain antibodies and VHH molecules, as well as anti-VL (e.g. V kappa (VK)) autoantibodies that can bind VL molecules" and that "[t]he pre-existing ADAs that bind VH dAbs are similar to anti-hinge antibodies in that they bind IgG fragments but not those same sequences found in situ on intact IgG."

Holland et al., J. Clin. Immunol. 2013, 33(7):1192-203 describe that the blood of around half of normal healthy humans contain varying levels of a new class of anti-IgG autoantibodies that can bind to the framework sequences of fully human $V_H$ domain antibodies (which Holland et al. also refer to as "HAVH auto-antibodies"). Holland et al. further mention that these auto-antibodies appear to be predominantly of the IgG isotype, display a relatively high affinity (about $10^{-10}$M) for $V_H$ sequences, and that a free C-terminus appears to be important for the binding of these HAVH autoantibodies to $V_H$ domains.

The pre-existing factors/antibodies referred to in the above and further prior art cited herein are also referred to herein by means of the general term "pre-existing antibodies". The issues relating to such pre-existing biotherapeutic-reactive antibodies against biotherapeutic molecules and their regulatory impact are also generally discussed by Xue et al., AAPS J. 2013; 15(3):852-5.

WO 12/175741 in Examples 7 and 8 also describes a monoclonal antibody called "21-4" (which is expressed by a hybridoma cell line called "ABH0015" that has been deposited on Jun. 4, 2012 with the BCCM, Ghent, Belgium) that recognizes the C-terminus of a NANOBODY® and that can be used in order to predict whether an ISV has a tendency to be bound by pre-existing antibodies (referred to in WO 12/175741 as "aspecific protein interference").

The aforementioned prior art has also focused on ways in which the sequence of an immunoglobulin variable domain may be modified so as to prevent or reduce binding of such pre-existing antibodies/factor(s) to the variable domains. In this respect, WO 2011/075861 suggests to make one or more mutations in the amino acid sequence of the variable domain at some specific positions of the domain (which positions are surface-exposed). WO 12/175741 describes that the binding of such pre-existing antibodies/factors may be reduced by adding a few amino acid residues (and as little as one alanine residue) to the C-terminal end of the VH-domain and/or by making one or more specific substitutions or deletions within the C-terminal region of the variable domain, which is described in WO 12/175741 as at least comprising the C-terminal amino acid sequence VTVSS (SEQ ID NO: 102) and the amino acid residue at position 14 (for which position WO 12/175741 teaches that the presence of an alanine residue provides for reduced binding of pre-existing antibodies as compared to the presence of the "human" amino acid residue proline), and possibly also the amino acid residues at positions 108 and 83 and amino acid residues close to said positions (WO 2013/024059 provides essentially the same teaching as WO 12/175741).

In addition, in the research leading up to the co-pending priority applications entitled "Improved immunoglobulin variable domains" (U.S. 61/994,552 filed May 16, 2014; U.S. 61/014,015 filed Jun. 18, 2014; U.S. 62/040,167 filed Aug. 21, 2014; and U.S. 62/047,560, filed Sep. 8, 2014; all assigned to Ablynx N.V. and which share some of the inventors with the present application. The PCT application WOO 2015/173325 based on these priority applications was published on Nov. 19, 2015), it was found that samples obtained from human subjects (healthy volunteers and/or subjects suffering from a disease or disorder) possibly contain (other) pre-existing antibodies or factors that can bind to the exposed C-terminal region of a NANOBODY® (or other VH domain) even when a C-terminal extension according to for example WO 12/175741 is present. In doing so, it was also found that, although essentially no such pre-existing antibodies binding to a C-terminally extended VH domain can be found in the blood or serum of healthy volunteers or in blood or serum obtained from human patients suffering from one of a number of different diseases (including some inflammatory diseases or auto-immune disorders—data not shown), some blood or serum samples that have been obtained from certain (but not all) human subjects suffering from certain severe auto-immune disorders (such as systemic lupus erythematosus; also abbreviated herein as "SLE") appear to contain some pre-existing antibodies/factors that can bind to NANOBODIES® even when said NANOBODIES® comprise a C-terminal extension.

Generally, the purpose of the present invention is to provide immunoglobulin variable domains (and in particular improved ISVD's) that are less prone to be bound by pre-existing antibodies, such as those found in blood or serum samples obtained from human subjects.

More in particular, the present invention aims to provide a technique for preventing and/or reducing (i.e. partially or essentially fully) the binding of pre-existing antibodies to immunoglobulin (single) variable domains and to polypeptides, proteins and other constructs or compounds comprising the same (in particular when, in the polypeptides etc., the immunoglobulin (single) variable domain(s) present have an exposed C-terminal end) that is an alternative to the use of the C-terminal extensions and/or framework mutations that have been used in the prior art cited herein (however, having said this, the use of such C-terminal extensions and/or mutations in suitable combination with the glycosylation of the invention is not excluded and falls within the broadest scope of the invention).

Generally, in the invention, the immunoglobulin (single) variable domains are glycosylated such that the glycosylation of the invention prevents pre-existing antibodies from binding to the exposed C-terminal end and/or such that the glycosylation of the invention reduces (i.e. substantially or preferably essentially fully) such binding.

In order to achieve this, the invention also provides glycosylation sites that can be introduced into immunoglobulin (single) variable domains so as to achieve such prevention or reduction of binding by pre-existing antibodies upon said glycosylation sites being glycosylated. In addition, in the research leading up to the present invention, it has been found that the glycosylation of the invention can also improve solubility and/or reduce immunogenicity.

The immunoglobulin variable domains that can be modified using the glycosylation of the invention are in particular immunoglobulin heavy chain variable domains (i.e. $V_H$ domains) and more in particular immunoglobulin heavy chain single variable domains (as further described herein), such as NANOBODIES® (including VHH's, humanized VHH's and camelized VH's such as camelized human VH's), (single) domain antibodies that are VH domains or derived from VH domains, and dAb's that are VH domains or derived from VH domains.

Thus, in a first aspect, the invention provides an immunoglobulin heavy-chain variable domain, and in particular an immunoglobulin heavy-chain single variable domain, which contains a glycosylation site such that the amino acid residue at one of positions 10, 11, 12, 13, 14, 39, 40, 41, 42, 87, 89, 108, 110, 112, 113 or 114, and in particular one of positions 11, 13, 87, 89, 108, 110, 112, 113 or 114 (numbering according to Kabat) is (or can be) glycosylated (for example, because said position contains an asparagine residue of a NXT or NXS motif, as further described herein).

According to a more preferred aspect, the invention provides an immunoglobulin heavy-chain variable domain, and in particular an immunoglobulin heavy-chain single variable domain, which contains a glycosylation site such that the amino acid residue at one of positions 108, 110, 112, 113 or 114 (numbering according to Kabat) is (or can be) glycosylated. In particular, of these positions, it has been found that glycosylation at position 108 is particularly effective in reducing/preventing binding of pre-existing antibodies (see the experimental data set out below).

According to another aspect, the invention provides an immunoglobulin heavy-chain variable domain, and in particular an immunoglobulin heavy-chain single variable domain, which contains a glycosylation site such that the amino acid residue at one of positions 108, 110, 112, 113 or 114 (numbering according to Kabat) is (or can be) glycosylated, and optionally also one or more of positions 10, 11, 12, 13, 14, 39, 40, 41, 42, 87 and/or 89 can be glycosylated.

More generally, the presence of a glycosylation site of the invention does not preclude that one or more other glycosylation sites are suitably present in the VH domain of the invention.

In the invention, the glycosylation will usually be N-linked glycosylation (and the invention will be further described and exemplified herein with reference to N-glycosylation), although the use of other kinds of glycosylation (such as O-linked glycosylation) is, although less preferred, not excluded from the scope of the invention in its broadest sense.

As is known to the skilled person, a glycosylation site for N-linked glycosylation will usually comprise an NXT motif or NXS motif (in which X can be any amino acid residue) which motif is glycosylated on the asparagine (N) residue. Thus, in the present specification, when it is stated that a position can be glycosylated, and it is intended that this position is N-glycosylated (which is preferred in the invention), then the primary sequence of the VH domain of the invention will generally contain an NXT or NXS motif (suitably introduced by mutating and/or substituting the relevant amino acid position(s)) such that the asparagine residue of said motif is present at the position to be glycosylated.

Thus, in another aspect, the invention provides an immunoglobulin heavy-chain variable domain, and in particular an immunoglobulin heavy-chain single variable domain, which contains an N-glycosylation site such that the amino acid residue at one of positions 10, 11, 12, 13, 14, 39, 40, 41, 42, 87, 89, 108, 110, 112, 113 or 114, and in particular one of positions 11, 13, 87, 89, 108, 110, 112, 113 or 114 (numbering according to Kabat), and in particular at one of the positions 108, 110, 112, 113 or 114, and more in particular at position 108, is an asparagine residue that is or can be N-glycosylated. In particular, such an immunoglobulin heavy-chain (single) variable domain may contain an NXT or NXS motif such that the asparagine residue of the NXT/NXS motif is present at one of positions 11, 13, 87, 89, 108, 110, 112, 113 or 114 (numbering according to Kabat), and in particular at one of the positions 108, 110, 112, 113 or 114, and more in particular at position 108. Again, as indicated herein, when one of the positions 108, 110, 112, 113 or 114 is or can be glycosylated in accordance with the invention, it is possible (but not required) that the VH domain of the invention suitably contains one or more further glycosylation sites (for example but without limitation, such that one of positions 10, 11, 12, 13, 14, 39, 40, 41, 42, 87 and/or 89 can be glycosylated).

When the asparagine residue of the NXT or NXS motif is at position 108 or 110, respectively, the tables in FIGS. 3 and 4, respectively, give preferred but non-limiting examples of the amino acid residues that can be present at the other amino acid positions of framework 4 of an ISV of the invention. Generally, these can suitably be any of the amino acid residues that can occur at the relevant position(s) in framework 4 of a human VH domain (in particular a human VH3 domain—see FIGS. 3 and 4) and/or in framework 4 of a VHH domain (see again FIGS. 3 and 4).

Also, although this is not required, ISV's of the invention (such as those with the asparagine residue of the NXT or NXS motif at position 10, 11, 12, 13, 14, 39, 40, 41, 42, 87, 89, 108 or 110) can contain a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I). Such a C-terminal extension can be as further described in WO 12/175741 or in the co-pending priority applications of assignee entitled "Improved immuno globulin variable domains" mentioned above (and the corresponding PCT application WO 2015/173325), and can for example comprise a C-terminal alanine residue.

When the NXT or NXS motif starts at position 112 or 113, the last 1 or last 2 amino acid residues of this motif, respectively, will form a C-terminal extension (i.e. extending beyond position 113). This is exemplified in FIGS. 5A and 5B, which also again mention some of the amino acid residues that can occur at the other positions within framework 4.

Furthermore, it is also possible that the entire NXT or NXS motif forms a C-terminal extension. This is exemplified in FIG. 6, which also again mention some of the amino acid residues that can occur at the other positions within framework 4. However, this may be less preferred than having the asparagine residue of the NXT to NXS motif at position 108, 110, 112 or 113, and in particular be less preferred than having the asparagine residue of the NXT to NXS motif at position 108.

In the invention, when position 110 is not part of the NXT or NXS motif, the amino acid residue at this position can also be K or Q (i.e. instead of the T that usually occurs in this position), as described in the co-pending priority applications of assignee entitled "Improved immunoglobulin variable domains" mentioned above (and the corresponding PCT application WO 2015/173325). Similarly, when position 112 is not part of the NXT or NXS motif, the amino acid residue at this position can also be K or Q (i.e. instead of the S that usually occurs in this position), as also described in these priority applications. The ISVs of the invention can also contain one or more (in suitable combination) of the other amino acid residues or mutations mentioned in these priority applications and PCT application. For example and without limitation, in the ISVs of the invention, position 11 can be L, V or K; position 14 can be A or P; position 41 can be A or P; and position 89 can be T, V or L. Generally, however, although the presence of the specific mutations described in the aforementioned co-pending priority applications and PCT application is not excluded and may even further contribute to preventing or reducing the binding of pre-existing antibodies, this will generally not be required to achieve the effect provided by the glycosylation of the invention.

In the invention, when one or more of positions 108 to 113 (and in particular one or more of positions 108, 110, 112 or 113) is mutated so as to include a glycosylation site of the invention, it is possible that the(se) mutation(s) to the amino acid sequence also per se make(s) a contribution to reducing the binding of pre-existing antibodies, and such a contributing effect is not excluded from the scope of the invention. Similarly, when the glycosylation site of the invention forms (part of) a C-terminal extension (e.g. when the N-glycosylation site is at positions 112-114, 113-115 or 114-116, as illustrated herein) it is also not excluded that the C-terminal extension that is provided by this glycosylation site per se makes a contribution to reducing the binding of pre-existing antibodies, and again such a contributing effect is not excluded from the scope of the invention.

FIGS. 7A to 7E give some preferred but non-limiting examples of possible framework 4 sequences with NXT or NXS motifs that can be present in the ISV's of the invention (SEQ ID NOs: 1 to 98). Other framework 4 sequences that can be used in the invention may have 1 or 2 (preferably only 1) "amino acid differences" with one of the sequences of SEQ ID NOs: 1 to 98, provided that such framework 4 sequence still contains an NXT or NXS motif and also allows the ISV to essentially retain its other desired properties. For this purpose, any such amino acid difference(s) will usually comprise substitution of said amino acid residue(s) with another amino acid residue mentioned in the tables shown in FIG. 3, 4, 5 or 6 (as applicable) for the same position in the sequence.

As can be seen from FIGS. 7A to 7E, one advantage of having an NXT motif at positions 108 to 110 (compared to having an NXS motif at these positions or an NXT or NXS motif at the other positions mentioned herein) may be that this retains the threonine (T) residue normally found at position 110 of human and camelid framework 4 sequences. Similarly, one advantage of having an NXS motif at positions 110 to 112 (compared to having an NXT motif at these positions or an NXT or NXS motif at the other positions mentioned herein) may be that this retains the serine (S) residue normally found at position 112 of human and camelid framework 4 sequences. However, although preferred, retaining the T110 or the S112, respectively, is not critical; for example, the data shown in the co-pending priority applications of assignee entitled "Improved immunoglobulin variable domains" mentioned above (and the corresponding PCT application) shows that positions 110 and 112 may also be substituted by other amino acid residues (in the case of these co-pending priority applications, a K or Q residue).

More generally, in the practice of the invention, the choice of the specific positions in which the NXT motif or NXS motif is introduced will often also be guided by the expression levels that can be obtained when the relevant ISV or compound is expressed in the desired host cell or host organism, as well as, when the host cell or host organism is chosen in order to glycosylate the expressed ISV or compound, the degree to which the desired level of glycosylation can be obtained.

In the immunoglobulin (single) variable domains of the invention, the asparagine residue of the NXT/NXS motif can be glycosylated or non-glycosylated. However, based on the disclosure herein, it will be clear to the skilled person that when the ISV (or a compound of the invention comprising the same) is in the final form for administration to a human subject and/or therapeutic use, it should be glycosylated so as to prevent binding of pre-existing antibodies when the ISV (or compound) enters the circulation.

In the NXT or NXS motif used as the N-glycosylation site in the invention, X can be any amino acid, but in the practice of the invention can in particular be an amino acid residue that naturally occurs at the relevant position in a VH or VHH domain and/or one of the amino acid residues mentioned for this position in any of FIG. 2, 3, 5, 5A, 5B or 6.

As will be clear to the skilled person, the glycosylation present on the asparagine residue (i.e. the oligosaccharide/glycan attached to the N-residue) will in practice often depend on the host cell or host organism that has been chosen to express/produce the ISV/compound. In general, any suitable glycosylation/oligosaccharide/glycan (either attached through chemical attachment or attached as a result of post-translational modification by the host cell/host organism used) can be used, as long as it is capable of reducing or preventing the binding of pre-existing antibodies (as can easily be determined by the skilled person, for example by using the experimental means described in the Experimental Part below; and/or by determining whether the glycosylated ISV/compound is bound by the monoclonal 21-4 described in WO 12/175741, which as mentioned can be used to predict whether an ISV or compound will be bound by pre-existing antibodies).

The host cell or host organism can be any suitable host cell or host organism that is capable of glycosylating the expressed IS V/compound of the invention. In particular, when the ISV/compound of the invention contains a suitable NXS or NXT motif, the host cell or host organism should be capable of N-glycosylating the asparagine residue in said motif. Also, when the expressed ISV/compound of the invention is intended for administration to a human subject and/or for therapeutic use, the host cell or host organism should generally be suitable for use in a manufacturing process (such as a GMP manufacturing process) that is to be used for the production of proteins (e.g. in the form of a drug substance, drug product or final formulation) that are suitable for administration to a human subject and/or for therapeutic use.

As will be clear to the skilled person, in the practice of the invention, the host cell or host organism will usually be a eukaryotic cell or organism, such as a mammalian cell or cell line or a suitable yeast cell (for example suitable strains *Pichia pastoris, Aspergillus niger* or *Saccharomyces cerevisiae*). Some preferred but non-limiting examples of suitable mammalian cell lines or yeast strains include (without limitation): Chinese Hamster Ovary (CHO) cells, Human embryonic kidney (HEK) cells, Sp2/0 or Ns0 mouse myeloma cells and baby hamster kidney (BHK) cells as well as other mammalian cell lines and yeast strains that can be used for the expression/production/manufacture of polypeptides and proteins that are intended for administration to human subjects and/or for therapeutic use. Generally, the use of suitable mammalian (and in particular human-derived) cells/cell lines will be preferred as this will result in glycosylated VH domains of the invention having "mammalian-type" (and in particular human-like) glycosylation. Alternatively, this may also be achieved by using modified/engineered yeast strains providing "mammalian-type" glycosylation (see for example Choi et al., PNAS, 2003, 5022-5027; Hamilton et al., Curr. Op. Biotechnol., 2007, 387-392 and Hamilton et al., Science, 2003, 1244-1246). Other suitable techniques for "glyco-engineering" of glycosylated products obtained from expression in yeast strains (and modified yeast strains for use in such techniques) can also be applied, such as those described in Laukens et al., Future Microbiol. 2015; 10(1):21-34; Meuris et al., Nat Biotechnol. 2014 May; 32(5):485-9; Tiels et al., Nat Biotechnol. 2012 December; 30(12):1225-31; De Pourcq et al., PLoS One. 2012; 7(6):e39976; De Pourcq et al., Microb Cell Fact. 2012 May 1; 11:53; Vervecken et al., Methods Mol Biol. 2007; 389:119-3; and other techniques reviewed by Jacobs and Callewaert N, Curr Mol Med. 2009 September; 9(7):774-800.

As the VH domains of the invention (and the proteins, polypeptides, compounds, constructs and other chemical entities comprising the same as further described herein) are particularly useful in (and intended for) pharmaceutical uses (such as the prevention, treatment and/or diagnosis of diseases and disorders in human subjects in need of the same), they preferably have a high degree of sequence homology in their framework regions with the framework sequences of human VH domains. In particular, the VH domains of the invention preferably have an overall degree of sequence identity (determined as further described herein, and taking into account only the framework regions and not the CDR's, and also not taking into account the substitution at position 112 and any C-terminal extension if present) with at least one human germline sequence (such as DP-47, DP-51 or DP-29) of at least 80%, preferably at least 85%, such as 90% or more. More in particular, the VH domains of the invention preferably have an overall degree of sequence identity (determined as further described herein, and taking into account only the framework regions and not the CDR's, and also not taking into account the substitution at position 112 and any C-terminal extension if present) of at least 80%, preferably at least 85%, such as 90% or more with at least one of the following human germline sequences: DP-47, DP-51 and/or DP-29.

As further described herein, according to one aspect of the invention, the VH domain of the invention can be a heavy-chain variable domain that, in the protein, polypeptide, protein or construct in which it is present, interacts/associates (or is intended to interact/associate) with a VL domain in order to form an antigen binding site, in which at least the VH domain has an exposed C-terminal end or region. For example, a VH domain according to this aspect of the invention can be a VH domain that is present and/or used in a ScFv and or a diabody, where it will associate with a VL domain to form an antigen binding site.

However, according to a preferred aspect of the invention, the VH domain of the invention is an (heavy-chain) immunoglobulin single variable domain or "ISVD", meaning a heavy-chain variable domain that can form a functional antigen binding site without interaction with a VL domain. For example, the VH domain of the invention can be a NANOBODY® (including a VHH, a humanized VHH and/or a camelized VHs such as camelized human VH's), a (single domain) antibody that is a VH domain or that is derived from a VH domain, or a dAb that is a VH domain or that is derived from a VH domain, or another VH domain that is suitable for use as an ISVD/(single) domain antibody. The VH domain of the invention is preferably a NANOBODY® (and more preferably a VHH domain, a humanized VHH domain or a camelized VH domain such as a camelized human VH domain).

In the present specification:

the term "NANOBODY®" is generally as defined in WO 08/020079 or WO 09/138519, and thus in a specific aspect generally denotes a VHH, a humanized VHH or a camelized VH (such as a camelized human VH) or generally a sequence optimized VHH (such as e.g. optimized for chemical stability and/or solubility, maximum overlap with known human framework regions and maximum expression). It is noted that the terms NANOBODY® or NANOBODIES® are registered trademarks of Ablynx N.V.;

the term "ISVD" (or "ISV") as used herein in its broadest sense also includes "ISVD-based biologicals" and, when the ISVD is a NANOBODY®, "Nanobody-based biologicals". An "ISVD-based biological" is defined herein as a protein, polypeptide or other biological drug that comprises or essentially consist of at least one (such as one, two or three) ISVD's. Similarly, a "Nanobody-based biological" is defined as a protein, polypeptide or other biological drug that comprises or essentially consist of at least one (such as one, two or three) NANOBODIES®. As with the term "ISVD", whenever the term "ISVD-based biological" is used, it should be understood that such an ISVD-based biological is preferably a Nanobody-based biological. Within the context of the present invention, both an "ISVD-based biological" and a "Nanobody-based biological" may for example be a monovalent, bivalent (or multivalent), bispecific (or multispecific), and biparatopic (or "multiparatopic) ISVD construct or NANOBODY® construct, respectively. Also, any ISVD-based or Nanobody-based biological may for example, in addition to the one or more (such as one, two or three) ISVD's or NANOBODIES®, optionally further comprise one or more (such as one or two) other further therapeutic moieties and/or one or more (such as one or two) other moieties that influence the pharmacokinetic or pharmacodynamic properties of the ISVD-based or Nanobody-based biological (such as its half-life). Suitable examples of such further therapeutic or other moieties will be clear to the skilled person, and for example generally can include any therapeutically active protein, polypeptide or other binding domain or binding unit, as well as for example modifications such as those described on pages 149 to 152 of WO 09/138159. An ISVD-based biological or Nanobody-based biological is preferably a therapeutic or intended for use as a therapeutic (which includes prophylaxis and diagnosis) and for this purpose preferably contains at least one ISVD against a therapeutically relevant target (such as for example RANK-L, vWF, IgE, RSV, CXCR4, IL-23 or other interleukins, etc.). For some specific but non-limiting examples of such ISVD-based or Nanobody-based biologicals, reference is for example made to the various applications by Ablynx N.V. (such as for example and without limitation WO 2004/062551, WO 2006/122825, WO 2008/020079 and WO 2009/068627), as well as for example (and without limitation) to applications such as WO 06/038027, WO 06/059108, WO 07/063308, WO 07/063311, WO 07/066016 and WO 07/085814. Also, as further described herein, an ISVD or NANOBODY® as described herein may be directed against a (human) serum protein such as (human) serum albumin, and such an ISVD or NANOBODY® may also find therapeutic uses, in particular in and/or for extending the half-life of therapeutic moieties and compounds (such as in or for the ISV-based biologicals described herein). Reference is for example made to WO 2004/041865, WO 2006/122787 and WO 2012/175400, which generally describe the use of serum-albumin binding NANOBODIES® for half-life extension. Also, in the present specification, unless explicitly mentioned otherwise herein, all terms mentioned herein have the meaning given in WO 09/138519 (or in the prior art cited in WO 09/138519) or WO 08/020079 (or in the prior art cited in WO 08/020079). Also, where a method or technique is not specifically described herein, it can be performed as described in WO 09/138519 (or in the prior art cited in WO 09/138519) or WO 08/020079 (or in the prior art cited in WO 08/020079).

Also, when used in the present specification or claims, the following terms have the same meaning as given on, and/or where applicable can be determined in the manner described in, pages 62-75 of WO 09/138519: "agonist", "antagonist", "inverse agonist", "non-polar, uncharged amino acid residue", "polar uncharged amino acid residue", "polar, charged amino acid residue", "sequence identity", "exactly the same" and "amino acid difference" (when referring to a sequence comparison of two amino acid sequences), "(in) essentially isolated (form)", "domain", "binding domain", "antigenic determinant", "epitope", "against" or "directed against" (an antigen), "specificity" and "half-life". In addition, the terms "modulating" and "to modulate", "interaction site", "specific for", "cross-block", "cross-blocked" and "cross-blocking" and "essentially independent of the pH" are as defined on (and/or can be determined as described on) pages 74-79 of WO 10/130832 of applicant. Also, when referring to a construct, compound, protein or polypeptide of the invention, terms like "monovalent", "bivalent" (or "multivalent"), "bispecific" (or "multispecific"), and "biparatopic" (or "multiparatopic") may have the meaning given in WO 09/138.519, WO 10/130832 or WO 08/020079.

The term "half-life" as used herein in relation to an ISVD, NANOBODY®, ISVD-based biological, Nanobody-based biological or any other amino acid sequence, compound or polypeptide referred to herein can generally be defined as described in paragraph o) on page 57 of WO 08/020079 and as mentioned therein refers to the time taken for the serum concentration of the amino acid sequence, compound or polypeptide to be reduced by 50%, in vivo, for example due to degradation of the sequence or compound and/or clearance or sequestration of the sequence or compound by natural mechanisms. The in vivo half-life of an amino acid sequence, compound or polypeptide of the invention can be determined in any manner known per se, such as by pharmacokinetic analysis. Suitable techniques will be clear to the person skilled in the art, and may for example generally be as described in paragraph o) on page 57 of WO 08/020079. As also mentioned in paragraph o) on page 57 of WO 08/020079, the half-life can be expressed using parameters such as the t1/2-alpha, t1/2-beta and the area under the curve (AUC). In this respect it should be noted that the term "half-life" as used herein in particular refers to the t1/2-beta or terminal half-life (in which the t1/2-alpha and/or the AUC or both may be kept out of considerations). Reference is for example made to the Experimental Part below, as well as to the standard handbooks, such as Kenneth, A et al: Chemical Stability of Pharmaceuticals: A Handbook for Pharmacists and Peters et al, Pharmacokinete analysis: A Practical Approach (1996). Reference is also made to "Pharmacokinetics", M Gibaldi & D Perron, published by Marcel Dekker, 2nd Rev. edition (1982). Similarly, the terms "increase in half-life" or "increased half-life" as also as defined in paragraph o) on page 57 of WO 08/020079 and in particular refer to an increase in the t1/2-beta, either with or without an increase in the t1/2-alpha and/or the AUC or both. When a term is not specifically defined herein, it has its usual meaning in the art, which will be clear to the skilled person. Reference is for example made to the standard handbooks, such as Sambrook et al, "Molecular Cloning: A Laboratory Manual" (2nd.Ed.), Vols. 1-3, Cold Spring Harbor Laboratory Press (1989); F. Ausubel et al, eds., "Current protocols in molecular biology", Green Publishing and Wiley Interscience, New York (1987); Lewin, "Genes II", John Wiley & Sons, New York, N.Y., (1985); Old et al., "Principles of Gene Manipulation: An Introduction to Genetic Engineering", 2nd edition, University of California Press, Berkeley, Calif. (1981); Roitt et al., "Immunology" (6th. Ed.), Mosby/Elsevier, Edinburgh (2001); Roitt et al., Roitt's Essential Immunology, 10th Ed. Blackwell Publishing, U K (2001); and Janeway et al., "Immunobiology" (6th Ed.), Garland Science Publishing/Churchill Livingstone, New York (2005), as well as to the general background art cited herein.

Also, as already indicated herein, the amino acid residues of a NANOBODY® are numbered according to the general numbering for VH domains given by Kabat et al. ("Sequence of proteins of immunological interest", US Public Health Services, NIH Bethesda, Md., Publication No. 91), as applied to VHH domains from Camelids in the article of Riechmann and Muyldermans, J. Immunol. Methods 2000 Jun. 23; 240 (1-2): 185-195; or referred to herein. According to this numbering, FR1 of a NANOBODY® comprises the amino acid residues at positions 1-30, CDR1 of a NANOBODY® comprises the amino acid residues at positions 31-35, FR2 of a NANOBODY® comprises the amino acids at positions 36-49, CDR2 of a NANOBODY® comprises the amino acid residues at positions 50-65, FR3 of a NANO- BODY® comprises the amino acid residues at positions 66-94, CDR3 of a NANOBODY® comprises the amino acid residues at positions 95-102, and FR4 of a NANOBODY® comprises the amino acid residues at positions 103-113. [In this respect, it should be noted that—as is well known in the art for VH domains and for VHH domains—the total number of amino acid residues in each of the CDR's may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. Generally, however, it can be said that, according to the numbering of Kabat and irrespective of the number of amino acid residues in the CDR's, position 1 according to the Kabat numbering corresponds to the start of FR1 and vice versa, position 36 according to the Kabat numbering corresponds to the start of FR2 and vice versa, position 66 according to the Kabat numbering corresponds to the start of FR3 and vice versa, and position 103 according to the Kabat numbering corresponds to the start of FR4 and vice versa.].

Alternative methods for numbering the amino acid residues of VH domains, which methods can also be applied in an analogous manner to VHH domains from Camelids and to NANOBODIES®, are the method described by Chothia et al. (Nature 342, 877-883 (1989)), the so-called "AbM definition" and the so-called "contact definition". However, in the present description, aspects and figures, the numbering according to Kabat as applied to VHH domains by Riechmann and Muyldermans will be followed, unless indicated otherwise.

It should also be noted that the Figures, any Sequence Listing and the Experimental Part/Examples are only given to further illustrate the invention and should not be interpreted or construed as limiting the scope of the invention and/or of the appended claims in any way, unless explicitly indicated otherwise herein.

As mentioned herein, the VH domains of the invention can be directed against any suitable or desired antigen or target, including any pharmaceutically and/or therapeutically relevant target as described herein.

Also, in the VH domains of the invention as defined herein, the amino acid residues at positions that are not explicitly defined herein can be any amino acid residue that is suitable at such a position for VH domains, and in particular for ISVD's and more in particular for NANOBODIES® (including humanized VHH domains). Reference is again made to the prior art cited herein, such as for example Tables A-3 and A-5 to A-8 of WO 08/020079, as well as FIG. 6. Preferably, in each case, the amino acid residue at position 11 is L or V, and more preferably V. Also: (i) position 41 may for example be one of the amino acid residues (i.e. human VH3 residues and/or Camelid VHH residues) mentioned in Table A-6 of WO 08/020079 for position 41 and may in particular be (or be chosen from) proline (P), serine (S), threonine (T), alanine (A) or leucine (L), which are some of the amino acid residues that most frequently occur at this position in either humans or llamas, and may more in particular be either proline (P) or alanine (A); and/or (ii) position 42 may for example be one of the amino acid residues (i.e. human VH3 residues and/or Camelid VHH residues) mentioned in Table A-6 of WO 08/020079 for position 42 and may in particular be (or be chosen from) glycine (G) or glutamic acid (E); (iii) position 87 may for example be one of the amino acid residues (i.e. human VH3 residues and/or Camelid VHH residues) mentioned in Table A-7 of WO 08/020079 for position 87 and may in particular be (or be chosen from) threonine (T) or alanine (A); (iv) position 89 may in particular be chosen from T, V or L; (v) position 110 (if not part of the glycosylation site of the invention) may be T, K or Q; and/or (iv) position 112 (if not part of the glycosylation site of the invention) may be S, K or Q.

According to one specific aspect of the invention, the VH domains of the invention are directed against a serum protein, and in particular a human serum protein. According to a preferred aspect, when a VH domain of the invention is directed against a serum protein, it is directed against serum albumin, and in particular human serum albumin. Thus, the invention also relates to a VH domain of the invention that can specifically bind to a serum protein, in particular a human serum protein, and that can preferably specifically bind to serum albumin, and more preferably to human serum albumin. Again, such a VH domain is preferably an ISVD (as described herein) and more preferably a NANOBODY®.

For example, a VH domain of the invention against serum albumin can be one of the NANOBODIES® against (human) serum albumin that are described in WO 2004/041865, and in particular in WO 2006/122787 and WO 2012/175400 (all applications from applicant/assignee), which has been provided with a glycosylation site of the invention (which may be non-glycosylated but is most preferably glycosylated when applied for final use in a human subject). Furthermore, it is envisaged that the present invention can also be applied to other serum-albumin binding heavy-chain ISVD's, such as those described in WO 03/035694, WO 04/003019, WO 05/118642, WO 06/059106, WO 08/096158, WO 09/121804, WO 10/108937 or US 2013/0129727, i.e. by suitably providing the same with a glycosylation site of the invention (which may be non-glycosylated but is most preferably glycosylated when applied for final use in a human subject).

Some preferred but non-limiting examples of such serum albumin binding NANOBODIES® of the invention are humanized variants of the amino acid sequence of SEQ ID NO: 52 of WO 2006/122787 (called "Alb-1" in WO 2006/122787), which have been provided with a glycosylation site of the invention (which may be non-glycosylated but is most preferably glycosylated when applied for final use in a human subject).

Thus, in a further aspect, the invention relates to a NANOBODY® of the invention (as defined herein) that can bind (and in particular specifically bind) to serum albumin (and in particular human serum albumin) in which:

```
CDR1 is the amino acid sequence
                                  (SEQ ID NO: 41)
SFGMS;

CDR2 is the amino acid sequence
                                  (SEQ ID NO: 42)
SISGSGSDTLYADSVKG;

CDR3 is the amino acid sequence
                                  (SEQ ID NO: 43)
GGSLSR;
``` which has been provided with a glycosylation site of the invention (which may be non-glycosylated but is most preferably glycosylated when applied for final use in a human subject).

As mentioned, the invention can also be applied to the VH domains (such as the serum albumin-binding VH domains) that are described in the co-pending priority applications of assignee entitled "Improved immuno globulin variable domains" mentioned above, i.e. by suitably providing the same with a glycosylation site of the invention (which may be non-glycosylated but is most preferably glycosylated when applied for final use in a human subject). More generally, as described herein, glycosylation of the invention can also suitably be combined with a C-terminal extension as described in said co-pending applications and/or with one or more mutations as described in said co-pending applications.

The glycosylation of the invention may be effective in preventing or reducing binding of any kind of pre-existing antibodies that may occur in (the circulation of) a human subject, including those referred to in WO 12/175741, WO 13/024059 and in Holland et al. (all cited above). The glycosylation of the invention may also be effective in preventing or reducing binding of pre-existing antibodies of the kind described in the co-pending priority applications of assignee entitled "Improved immunoglobulin variable domains" mentioned above and the corresponding PCT application WO 2015/173325 (i.e. those that can bind to the exposed C-terminal end of a VH domain even in the presence of a C-terminal extension), even without a C-terminal extension or the specific mutations described in said co-pending applications being present.

Generally, in the context of the present application, by "reducing" or "reduced" binding of pre-existing antibodies, in particular the following is meant: a reduction of binding by pre-existing antibodies (calculated by the method described in Example 3 based on binding data obtained for a set of relevant serum samples, which binding data is measured for each sample using the techniques described in the Experimental Part below) of at least 10%, preferably at least 25%, more preferably at least 50%, such as more than 75%, compared to a suitable reference.

Also generally, in the context of the present invention, when the binding of a glycosylated immunoglobulin (single) variable domain of the invention is said to be reduced "compared to the same immunoglobulin (single) variable domain without the glycosylation according to the invention being present", said binding can be reduced compared to either:
a) an immunoglobulin (single) variable domain with the exactly same sequence (i.e. including the glycosylation site of the invention) but without the glycosylation of the invention being present (i.e. meaning the corresponding immunoglobulin (single) variable domain of the invention in which the glycosylation site of the invention is not glycosylated); and/or
b) an immunoglobulin (single) variable domain with the exactly same sequence but without the glycosylation site of the invention being present. As will be clear to the skilled person, this will usually be the (starting) sequence to which the method of the invention is applied (i.e. in which a glycosylation site of the invention is introduced) in order to reduce or prevent binding of pre-existing antibodies to said starting immunoglobulin (single) variable domain. For example, when an asparagine residue is introduced at position 108 to introduce an NXT or NXS motif, respectively, in a starting sequence, the "exact same sequence but without the glycosylation site of the invention being present" may be the (starting) sequence in with the amino acid residue at position 108, is the amino acid residue that was present at said position before the asparagine residue was introduced; or compared to both a) and b).

In order to compare the binding of pre-existing antibodies to the final glycosylated immunoglobulin (single) variable domain to the binding of pre-existing antibodies to the comparator immunoglobulin (single) variable domain(s), the calculation method described in Example 3 below can be used (based on binding data obtained for a set of relevant serum samples, which binding data is measured for each sample using the techniques described in the Experimental Part below). Preferably, using said calculation, binding by pre-existing antibodies is reduced by at least 10%, preferably by at least 25%, more preferably by at least 50%, such as by more than 75%, compared to a non-glycosylated reference.

Similarly, in the context of the present invention, when the binding of a glycosylated compound of the invention is said to be reduced "compared to the same compound of the invention without the glycosylation according to the invention being present", said binding can be reduced compared to either:
a) a compound with the exactly same sequence (i.e. including the glycosylation site of the invention) but without the glycosylation of the invention being present (i.e. meaning the compound of the invention in which the glycosylation site of the invention is not glycosylated); and/or
b) a compound with the exactly same sequence but without the glycosylation site of the invention being present (i.e. as indicated above). As will be clear to the skilled person, this will usually be the (starting) sequence to which the method of the invention is applied (i.e. in which a glycosylation site of the invention is introduced) in order to reduce or prevent binding of pre-existing antibodies to said starting compound;
or compared to both a) and b).

In order to compare the binding of pre-existing antibodies to the final glycosylated compound of the invention to the binding of pre-existing antibodies to the comparator compound, the same assay can be used as described above, and again preferably, in this assay, the reduction provided by the glycosylation of the invention (i.e. again compared to the comparator(s)) is at least at least 10%, preferably at least 25%, more preferably at least 50%, such as at least 75%, compared to a non-glycosylated reference.

The invention also relates to proteins, polypeptides, constructs, compounds or other chemical entities that comprise at least one VH domain of the invention (also collectively referred to herein as "compounds of the invention").

As further described herein, according to one specific but non-limiting aspect, in a compound of the invention, the VH domain of the invention is present at/forms the C-terminal end of the same. In such a case, the VH domain of the invention that forms/is present at the C-terminal end of the compound of the invention preferably is glycosylated as described herein.

As also further described herein, the compounds of the invention can be a ScFv, diabody or another protein, polypeptide or construct in which the one or more VH domains of the invention are associated with one or more VL domains to form one or more functional antigen-binding sites.

However, according to a preferred aspect of the invention, the VH domains of the invention are ISVD's and the compounds of the invention are proteins, polypeptides, constructs, compounds or other chemical entities that comprise or essentially consist of at least one ISVD of the invention and optionally one or more further amino acid sequences, moieties, binding domains or binding units (suitably linked to each other, optionally via one or more linkers). In particular, such compounds of the invention can comprise or essentially consist of one or more ISVD's, at least one of which is an ISVD of the invention. Such a compound of the invention may in particular have an ISVD of the invention at its C-terminal end, in which case the ISVD of the invention is preferably glycosylated as described herein. Also, if such a compound of the invention contains two or more ISVDs, two or more or essentially all of the ISVD's present may be glycosylated according to the invention. Also, in such a compound of the invention, the ISVD of the invention is preferably a NANOBODY® of the invention, and all or essentially all of the ISVD's present in the compound of the invention may be (and preferably are) NANOBODIES®. Examples of such compounds of the invention will be clear to the skilled person based on the further disclosure herein.

Some non-limiting examples of proteins, polypeptides, constructs, compounds or other chemical entities that comprise one or more ISVD's (including at least one ISVD of the invention) are multivalent, multispecific (such as bispecific) or multiparatopic (such as biparatopic) constructs that contain two or more ISVD's linked directly or via one or more suitable linkers. Again, the ISVD's are preferably NANOBODIES®. For some non-limiting examples of such constructs and a general teaching on how such constructs can be made (in particular based on NANOBODIES®) reference is for example made to Conrath et al., JBC 276, 10(9), 7346 (2001) as well as to the review article by Muyldermans. Reviews in Mol. Biotechnol., 74: 27 (2001).

For example, such a compound of the invention containing two or more ISVD's (at least one of which is an ISVD of the invention) may be a bivalent, trivalent, tetravalent or pentavalent construct, and/or may be a monospecific, bispecific, trispecific construct, and/or may be a biparatopic or triparatopic construct. Reference is again made to the prior art on ISVD-based and Nanobody-based biologicals cited herein. Also, such a compound of the invention may have been provided with an increased half-life by functionalization and/or by including in the construct a moiety or binding unit that increases the half-life of the construct. Examples of such functionalization, moieties or binding units will be clear to the skilled person and may for example be as described herein, and for example may include pegylation, fusion to serum albumin, or fusion to a peptide or binding unit that can bind to a serum protein such as serum albumin. Such a serum-albumin binding peptide or binding domain may be any suitable serum-albumin binding peptide or binding domain capable of increasing the half-life of the construct (compared to the same construct without the serum-albumin binding peptide or binding domain), and may in particular be serum albumin binding peptides as described in WO 2008/068280 by applicant (and in particular WO 2009/127691 and the non-prepublished U.S. application 61/301,819, both by applicant), or a serum-albumin binding ISV (such as a serum-albumin binding NANOBODY®; for example Alb-1 or a humanized version of Alb-1 such as Alb-8, for which reference is for example made to WO 06/122787), or an ISVD of the invention that is directed against a (human) serum protein such as (human) serum albumin (as further described herein). Generally, any compound of the invention with increased half-life will preferably have a half-life (as defined herein) in human subjects of at least 1 day, preferably at least 3 days, more preferably at least 7 days, such as at least 10 days.

When the compound of the invention comprises at least one (and preferably one) ISVD of the invention (and in particular NANOBODY® of the invention) that is directed against a (human) serum protein and in particular against (human) serum albumin, the compound of the invention will usually further contain one or more other therapeutically active amino acid sequences, moieties, binding domains or binding units (i.e. directed against a therapeutically relevant target, pathway or mechanism), and the ISVD of the invention will function to extend the half-life of the same (and of the entire compound). Again, said one or more further therapeutically active moieties are preferably ISVD's (and more preferably NANOBODIES®), and may also be IVSD's of the invention (and more preferably NANOBODIES® of the invention). In such compounds of the invention, the ISVD of the invention that is directed against human serum albumin may again be present at/forms the C-terminal end of the compound, and in that case may (and preferably is) glycosylated as described herein. When a compound of the invention contains an ISVD of the invention that is directed against (human) serum albumin, said the compound of the invention preferably has a half-life (as defined herein) of at least 1 day, preferably at least 3 days, more preferably at least 7 days, such as at least 10 days in the human subject to which the same is/has been administered. Some non-limiting examples of ISVD's of the invention against human serum albumin that can be used for this purpose are as further described herein. Also, when a compound of the invention contains a half-life extending ISVD, the glycosylation of the invention may (further) contribute to the increase in half-life.

In one aspect, all of the ISVD's or NANOBODIES® present in said compound of the invention are glycosylated according to the invention. However, it may be sufficient that only one of the ISVD's is glycosylated, in particular when said ISVD forms the C-terminal end of the compound of the invention.

Thus, in a further aspect, the invention relates to a protein, polypeptide or other compound or molecule that comprises or essentially consists of an ISVD of the invention (as further described herein). As described herein, said ISVD will contain a glycosylation site of the invention, which may be glycosylated or non-glycosylated, and is preferably glycosylated when it is in the (final) form intended for administration to a human subject.

The invention further relates to a protein, polypeptide or other compound or molecule that comprises at least one ISVD of the invention and at least one other therapeutic moiety or entity (either linked directly or via a suitable linker).

The invention further relates to a protein, polypeptide or other compound or molecule that comprises at least one ISVD of the invention that is directed against a (human) serum protein (and preferably against human serum albumin) and at least one other therapeutic moiety or entity (either linked directly or via a suitable linker).

The invention further relates to a protein, polypeptide or other compound or molecule that comprises at least two (such as two, three or four) immunoglobulin single variable domains (either linked directly or via a suitable linker), at least one of which is an ISVD of the invention. In this aspect: (i) the ISVD's present may suitably be the same or different; and when they are different they may be directed against the same target (for example, they may have different sequences and/or be directed against different epitopes on the same target) or against two or more different targets (i.e. such that the resulting protein, polypeptide or other compound or molecule is a bi- or multispecific construct); and/or (ii) the ISVD present at the C-terminal end of the protein, polypeptide or other compound or molecule may or may not be an ISVD of the invention (but preferably is); and/or (iii) when an ISVD of the invention is present at the C-terminal end of the protein, polypeptide or other compound or molecule, it preferably is glycosylated as described herein; and/or (iv) essentially all of the ISVD's present in the protein, polypeptide or other compound or molecule may be ISVD's of the invention. Also, when the ISVD's are directed against different targets (as least one of which is a therapeutic target), according to one further aspect at least one of the ISVD's present may be directed against a (human) serum protein such as human serum albumin (and this ISVD may or may not be an ISVD of the invention; and when it is an ISVD of the invention, it is preferably a NANOBODY® against human serum albumin that is as further described herein).

The invention further relates to such a protein, polypeptide or other compound or molecule that comprises or essentially consists of two immunoglobulin single variable domains (either linked directly or via a suitable linker).

The invention further relates to such a protein, polypeptide or other compound or molecule that comprises or essentially consists of three immunoglobulin single variable domains (either linked directly or via a suitable linker).

The invention further relates to such a protein, polypeptide or other compound or molecule comprises or essentially consists of four immunoglobulin single variable domains (either linked directly or via a suitable linker).

The invention further relates to such a protein, polypeptide or other compound or molecule that further comprises at least one moiety, binding domain or binding unit that confers an increased half-life to said protein, polypeptide or other compound or molecule (i.e. compared to the corresponding protein, polypeptide or other compound or molecule without said moiety, binding domain or binding unit). According to a more specific aspect, said at least one moiety, binding domain or binding unit that confers an increased half-life to said protein, polypeptide or other compound or molecule is an immunoglobulin single variable domain, more in particular an immunoglobulin single variable domain that is directed against a serum protein (such as serum albumin), and in particular against a human serum protein (such as human serum albumin); and as described herein may in particular be an ISVD of the invention. Said ISVD of the invention against the serum protein may be at the N-terminal end of the protein, polypeptide or other compound or molecule, at the C-terminal end, or (if the protein, polypeptide or other compound or molecule comprises more than two ISVD's) in the middle of the molecule.

The invention further relates to such a protein, polypeptide or other compound or molecule comprises or essentially consists of either:

two immunoglobulin single variable domains (either linked directly or via a suitable linker), i.e. (said) one immunoglobulin single variable domain (such as a NANOBODY®) that confers an increased half-life and one other immunoglobulin single variable domain (such as a NANOBODY®) that may in particular be directed against a therapeutic target;

three immunoglobulin single variable domains (either linked directly or via a suitable linker), i.e. (said) one immunoglobulin single variable domain (such as a NANOBODY®) that confers an increased half-life and two other immunoglobulin single variable domains (such as two other NANOBODIES®) that may in particular be directed against a therapeutic target (in which said two other immunoglobulin single variable domains may be directed against the same target, against two different targets or against two different epitopes on the same target); or four immunoglobulin single variable domains (either linked directly or via a suitable linker), i.e. (said) one immunoglobulin single variable domain (such as a NANOBODY®) that confers an increased half-life and two other immunoglobulin single variable domains (such as two other NANOBODIES®) that may in particular be directed against a therapeutic target (in which said three other immunoglobulin single variable domains may be directed against the same target, against two or three different targets and/or against two or three different epitopes on the same target).

Again, in such a protein, polypeptide or other compound or molecule: (i) the ISVD's present may suitably be the same or different; and when they are different they may be directed against the same target (for example, they may have different sequences and/or be directed against different epitopes on the same target) or against two or more different targets (i.e. such that the resulting protein, polypeptide or other compound or molecule is a bi- or multispecific construct); and/or (ii) the ISVD present at the C-terminal end of the protein, polypeptide or other compound or molecule may or may not be an ISVD of the invention (but preferably is); and/or (iii) when an ISVD of the invention is present at the C-terminal end of the protein, polypeptide or other compound or molecule, it is preferably glycosylated according to the invention; and/or (iv) essentially all of the ISVD's present in the protein, polypeptide or other compound or molecule may be ISVD's of the invention.

The invention further relates to methods for expressing/producing/manufacturing the VH domains of the invention and the compounds of the invention (as further described herein). For example, a VH domain of the invention can be expressed/produced by suitably expressing a nucleic acid that encodes the same in a suitable host organism. Reference is for example made to WO 08/020079 (as well as to some of the other patent applications of applicant/assignee cited herein), that generally describes suitable methods and techniques for expressing/producing NANOBODIES®, which methods can also suitably be used to express/produce NANOBODIES® of the invention. Methods for expressing VH domains of the invention other than NANOBODIES® will also be clear to the skilled person based on the disclosure and prior art cited herein. Compounds of the invention can be suitably manufactured/produced by suitably linking (usually via covalent bonds) one or more VH domains of the invention to the one or more further amino acid residues (and/or other groups or moieties) that are to be present in the final compound of the invention, optionally via one or more linkers or spacers. Alternatively, when a compound of the invention is a protein or polypeptide, it can be manufactured/produced by suitably expressing a nucleic acid that encodes the same in a suitable host organism. Reference is again for example made to the general methods described in WO 08/020079 and in some of the other patent applications of applicant/assignee cited herein.

As further described herein, in one specific aspect of the invention, the host cell or host organism is such that it can glycosylate the expressed ISVD or compound of the invention, so as to provide a glycosylated ISVD or compound of the invention.

The invention also relates to a nucleotide sequence and/or nucleic acid that encodes a VH domain of the invention or a compound of the invention. Such a nucleic acid can be DNA or RNA; and is preferably DNA and can be in the form of a plasmid or vector. Reference is again for example made to WO 08/020079 and to some of the other patent applications of applicant/assignee cited herein. The nucleotide sequence/nucleic acids may also be codon-optimized for the host cell or host organism that is to be used to express it, and according to a preferred aspect may in particular be codon-optimized for a host cell or host organism that is chosen because it can glycosylate the expressed sequence.

The invention also relates to a composition that comprises at least one VH domain of the invention, compound of the invention or nucleic acid encoding either of the same.

The invention further relates to a pharmaceutical composition that comprises an ISV (and preferably a therapeutic ISV) or a protein or polypeptide comprising at least one ISV (and preferably at least one therapeutic ISV), wherein said ISV, protein or polypeptide is as further described herein (i.e. an ISV, protein or polypeptide according to one or more of the aspects described herein, and in particular according to one or more of the aspects described on the preceding pages; and more in particular an ISV, protein or polypeptide that is glycosylated at its C-terminal end/according to one or more of the aspects described herein), and at least one suitable carrier, diluent or excipient (i.e. suitable for pharmaceutical use), and optionally one or more further active substances. Such compositions, carriers, diluents or excipients can for example be as described in WO 08/020079 for pharmaceutical compositions that comprise a NANOBODY® or a protein or polypeptide that comprises at least one NANOBODY® (and as already mentioned, according to the present invention, the ISV is also preferably a NANOBODY®).

The invention further relates to an ISV or a protein or polypeptide comprising at least one ISV for use in therapy of a disease in a human being (e.g. a patient in need of such therapy), wherein said ISV, protein or polypeptide is as further described herein (i.e. an ISV, protein or polypeptide according to one or more of the aspects described herein, and in particular according to one or more of the aspects described on the preceding pages; and more in particular an ISV, protein or polypeptide that at its C-terminal end is glycosylated according to one or more of the aspects described herein).

The invention further relates to the use of an ISV or a protein or polypeptide comprising at least one ISV in the preparation of a pharmaceutical composition, wherein said ISV, protein or polypeptide is as further described herein (i.e. an ISV, protein or polypeptide according to one or more of the aspects described herein, and in particular according to one or more of the aspects described on the preceding pages; and more in particular an ISV, protein or polypeptide that at its C-terminal end is glycosylated according to one or more of the aspects described herein).

The invention further relates to a method of treatment which comprises administering to a human subject (e.g. to a patient in need of such treatment) an ISV or a protein or polypeptide comprising at least one ISV in the preparation of a pharmaceutical composition, wherein said ISV, protein or polypeptide is as further described herein (i.e. an ISV, protein or polypeptide according to one or more of the aspects described herein, and in particular according to one or more of the aspects described on the preceding pages; and more in particular an ISV, protein or polypeptide that at its C-terminal end is glycosylated according to one or more of the aspects described herein); or a pharmaceutical composition (as described above) that comprises at least one such ISV, protein or polypeptide.

With respect to the above, it will be clear that the therapeutic use of the ISV's, proteins and polypeptides described herein are a very important aspect of the invention, as such therapeutic use (or the clinical development of such ISV's, proteins and polypeptides for such therapeutic use) may involve the use of ADA assays to determine whether said ISV, protein or polypeptide is immunogenic (i.e. can give rise to ADA's when administered to a human subject). In this respect, it will also be clear that concerns about possible immunogenicity will in particular have to be addressed when a therapeutic is either used for longer periods of time (for during weeks, months or years), and/or has a half-life (preferably expressed as t1/2-beta) in a human subject of at least 3 days, such as at least one week, and up to 10 days or more.

Thus, according to one specific aspect, the invention relates to an ISV, protein, polypeptide, compound or molecule of the invention as described herein (or pharmaceutical composition the same) that is intended for treatment of a chronic disease in a human being, and/or such ISV, protein, polypeptide as described herein is intended to be present in the circulation of the subject (i.e. at pharmacologically active levels) to which it is administered (i.e. at a therapeutically active dose) for at least a period of one week, preferably at least two weeks, such as at least a months; and/or such ISV, protein, polypeptide as described herein is such that it has a half-life (preferably expressed as t1/2-beta) in a human subject of at least 3 days, such as at least one week, and up to 10 days or more; and/or such an ISV, protein, polypeptide or pharmaceutical composition as described herein is intended to be administered to a human being as two or more doses that are administered over a period of at least 3 days, such as at least one week, for example at least two weeks or at least one month, or even longer (i.e. at least 3 months, at least 6 months or at least one year), or even chronically administered.

According to one specific aspect, the invention relates to an ISV, protein, polypeptide, compound or molecule of the invention as described herein (or a pharmaceutical composition the same) that is intended for administration to a human subject whose blood contains pre-existing antibodies that can bind to the exposed C-terminal region of a VH domain even when said VH-domain contains a C-terminal extension as described in WO 12/175741 (or where the C-terminal end of the VH domain is linked to another protein or polypeptide, such as another ISV, optionally via a suitable linker).

In particular, the invention relates to an ISV, protein, polypeptide, compound or molecule of the invention as described herein (or a pharmaceutical composition the same) for use in the treatment of a disease or disorder in a human subject whose blood contains pre-existing antibodies. Said disease or disorder can be any disease or disorder that can or is to be treated with the administered ISV, protein, polypeptide, compound or molecule of the invention.

As will be clear to the skilled person, when a protein, polypeptide, compound or molecule is intended for the prevention or treatment of such a disease or disorder, it will contain at least one (such as one, two, three or four) domains, binding units or moieties or entities that are therapeutically active against the relevant disease or disorder (e.g. directed against a target or pathway that is therapeutically relevant for the pertinent disease or disorder). Again, such binding domains or binding units may for example be (other) ISVD's, and according to one aspect may in particular be VH domains or ISVD's of the invention. Another general example of such a protein, polypeptide, compound or molecule is a protein, polypeptide, compound or molecule in which said one or more therapeutic domains, binding units or moieties or entities may not be ISVD's (but for example derived from another scaffold), but that contains a VH domain of the invention to extend the half-life of the same (such as a serum albumin binder as described herein).

According to one specific aspect, the invention relates to an ISV, protein, polypeptide, compound or molecule of the invention as described herein (or a pharmaceutical composition the same) that is intended for administration to a human subject whose blood contains pre-existing antibodies that can bind to the exposed C-terminal region of a VH domain even when said VH-domain contains a C-terminal extension as described in WO 12/175741 (or where the C-terminal end of the VH domain is linked to another protein or polypeptide, such as another ISV, optionally via a suitable linker).

In particular, the invention relates to an ISV, protein, polypeptide, compound or molecule of the invention as described herein (or a pharmaceutical composition the same) for use in the treatment of a disease or disorder in a human subject whose blood contains pre-existing antibodies that can bind to the exposed C-terminal region of a VH domain even when said VH-domain contains a C-terminal extension as described in WO 12/175741 (or where the C-terminal end of the VH domain is linked to another protein or polypeptide, such as another ISV, optionally via a suitable linker). Said disease or disorder can be any disease or disorder, but can in particular be a disease or disorder that leads to, results into or otherwise is associated with the presence of such pre-existing antibodies in the blood of such a patient, such as SLE or another (severe) autoimmune disease.

Thus, according to a more specific aspect, the invention relates to an ISV, protein, polypeptide, compound or molecule of the invention as described herein (or a pharmaceutical composition the same) for use in the treatment of a disease or disorder in a human subject/patient, wherein said disease or disorder is a disease or disorder that leads to, results into or otherwise is associated with the presence of pre-existing antibodies in the blood of said human subject/patient that can bind to the exposed C-terminal region of a VH domain even when said VH-domain contains a C-terminal extension as described in WO 12/175741 (or where the C-terminal end of the VH domain is linked to another protein or polypeptide, such as another ISV, optionally via a suitable linker). For example, such an ISV, protein, polypeptide, compound or molecule of the invention as described herein (or a pharmaceutical composition the same) for use in the treatment of SLE or another (severe) autoimmune disease in a human subject/patient.

As will be clear to the skilled person, when a protein, polypeptide, compound or molecule is intended for the prevention or treatment of such a disease or disorder, it will contain at least one (such as one, two, three or four) domains, binding units or moieties or entities that are therapeutically active against the relevant disease or disorder (e.g. directed against a target or pathway that is therapeutically relevant for the pertinent disease or disorder). Again, such binding domains or binding units may for example be (other) ISVD's, and according to one aspect may in particular be VH domains or ISVD's of the invention. Another general example of such a protein, polypeptide, compound or molecule is a protein, polypeptide, compound or molecule in which said one or more therapeutic domains, binding units or moieties or entities may not be ISVD's (but for example derived from another scaffold), but that contains a VH domain of the invention to extend the half-life of the same (such as a serum albumin binder as described herein).

The invention will now be further illustrated by means of the non-limiting Experimental Part below, as well as by means of the attached non-limiting Figures, in which:

FIG. 1 is a table comparing the numbering according to Kabat, Chothia, Aho and IMGT of some of the amino acid positions/residues in a VH or VHH domain that are specifically referred to herein;

FIG. 2 is a table that mentions some of the most prominent amino acid residues that can occur at the mentioned positions of framework 4 of a human VH domain and a Camelid VHH;

FIG. 3 is a table that mentions some of the most prominent amino acid residues (e.g. derived from a VH domain, a VHH domain or specific mutations) that can occur at the mentioned positions of framework 4 of an ISVD of the invention with an NXS or NXT motif at positions 108-110;

FIG. 4 is a table that mentions some of the most prominent amino acid residues (e.g. derived from a VH domain, a VHH domain or specific mutations) that can occur at the mentioned positions of framework 4 of an ISVD of the invention with an NXS or NXT motif at positions 110-113;

Figure 9:
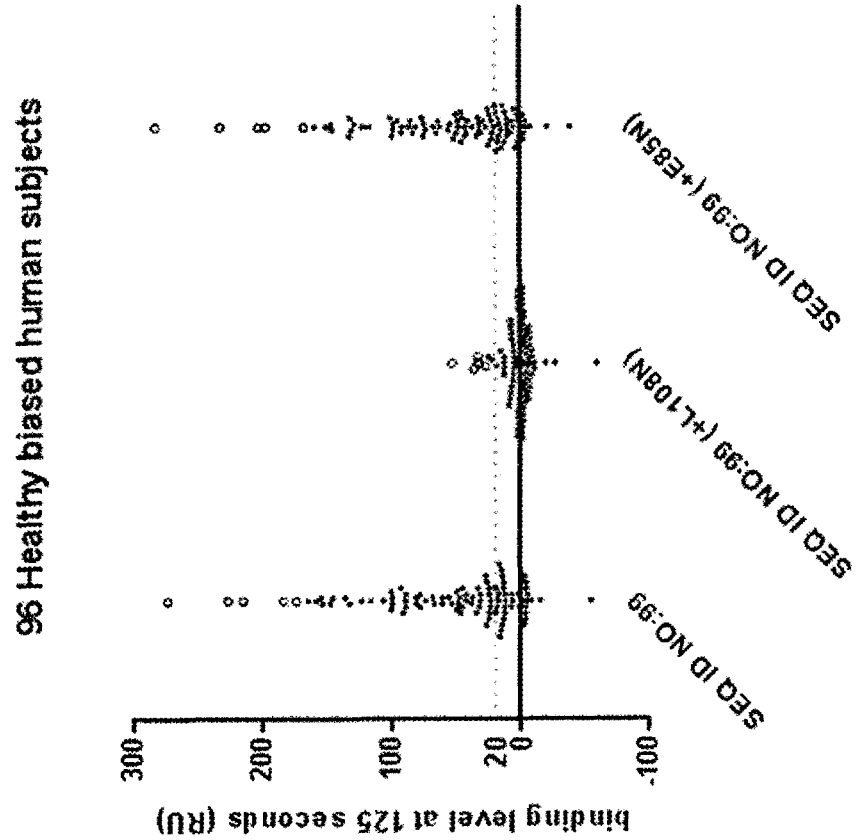
Figure 10:
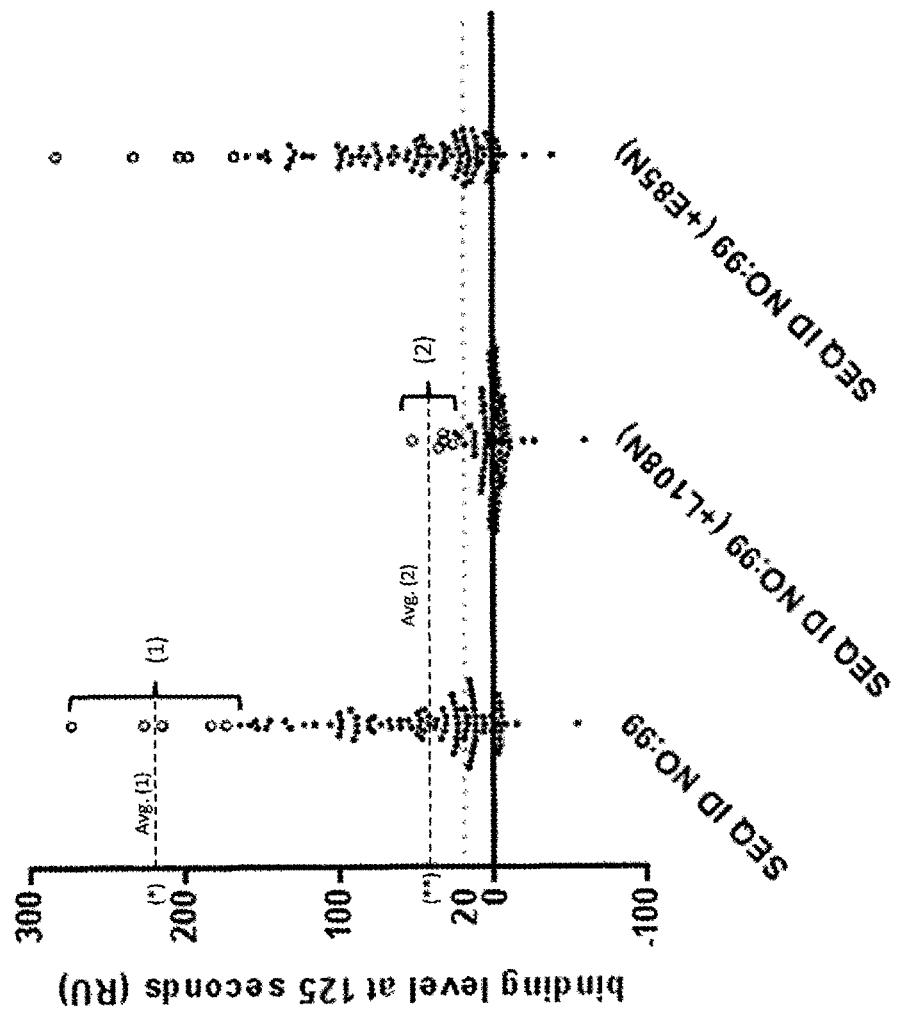

FIGS. 5A and 5B are tables that mention some of the most prominent amino acid residues (e.g. derived from a VH domain, a VHH domain or specific mutations) that can occur at the mentioned positions of framework 4 of an ISVD of the invention with an NXS or NXT motif at positions 112-114 (FIG. 5A) or positions 113-115 (FIG. 5B);

FIG. 6 is a table that mention some of the most prominent amino acid residues (e.g. derived from a VH domain, a VHH domain or specific mutations) that can occur at the mentioned positions of framework 4 of an ISVD of the invention with an NXS or NXT motif at positions 113-115 (i.e. as a C-terminal extension to the C-terminal end);

FIGS. 7A to 7D give some preferred but non-limiting examples of FR4 sequences that can be present in ISVD's of the invention with an NXS or NXT motif at positions 108-110 (FIG. 7A); in ISVD's of the invention with an NXS or NXT motif at positions 110-112 (FIG. 7B); in ISVD's of the invention with an NXS or NXT motif at positions 112-114 (FIG. 7C); in ISVD's of the invention with an NXS or NXT motif at positions 113-115 (FIG. 7D) and in ISVD's of the invention with an NXS or NXT motif at positions 114-116 (FIG. 7E);

FIG. 8 is a table listing some of the other amino acid sequences used in the present description;

FIG. 9 is a plot showing data points obtained in Example 2 when 96 serum samples from human volunteers were tested for binding to the ISVDs of SEQ ID NO: 99 (reference, no glycosylation site); SEQ ID NO: 100 (invention, glycosylation site at positions 108-110); and SEQ ID NO: 101 (comparative, glycosylation site at positions 85-87). In FIG. 9, the left hand graph shows normalized data; and the right hand graph shows the corresponding correlation graph for the same data points;

FIG. 10 schematically illustrates (using the data shown in FIG. 9 and Table II) how the reduction in binding by pre-existing antibodies can be determined and calculated using the method described in Example 3.

EXPERIMENTAL PART

The human samples used in the Experimental Part below were either obtained from commercial sources or from human volunteers (after all required consents and approvals were obtained) and were used in according with the applicable legal and regulatory requirements (including but not limited to those regarding medical secret and patient privacy).

In the Examples below, the binding of pre-existing antibodies that are present in the samples used (obtained from healthy volunteers) to the NANOBODIES® tested was determined using ProteOn as follows (these are essentially the same techniques, conditions and protocol as used in the Experimental Part of applicant's co-pending US priority applications entitled "Improved immuno globulin variable domains" referred to herein). Binding of pre-existing antibodies on NANOBODIES® captured on human serum albumin (HSA) was evaluated using the ProteOn XPR36 (Bio-Rad Laboratories, Inc.). PBS/Tween (phosphate buffered saline, pH7.4, 0.005% Tween20) was used as running buffer and the experiments were performed at 25° C. The ligand lanes of a ProteOn GLC Sensor Chip were activated with EDC/NHS (flow rate 30 μl/min) and HSA was injected at 10 μg/ml in ProteOn Acetate buffer pH4.5 (flow rate 100 μl/min) to render immobilization levels of between approximately 3000 RU and approximately-4000 RU (such as about 3200 or 3600 RU). After immobilization, surfaces were deactivated with ethanolamine HCl (flow rate 30 μl/min). NANOBODIES® were injected for 2 minutes at 45 μl/min over the HSA surface to render a NANOBODY® capture level of between approximately 175 RU and approximately 275 RU (such as about 200 or 250 RU). The samples containing pre-existing antibodies were centrifuged for 2 minutes at 14,000 rpm and supernatant was diluted 1:10 in PBS-Tween20 (0.005%) before being injected for 2 minutes at 45 μl/min followed by a subsequent 400 seconds dissociation step. After each cycle (i.e. before a new NANOBODY® capture and blood sample injection step) the HSA surfaces were regenerated with a 2 minute injection of HCl (100 mM) at 45 μl/min. Sensorgram processing and data analysis was performed with ProteOn Manager 3.1.0 (Bio-Rad Laboratories, Inc.). Sensorgrams showing pre-existing antibody binding were obtained after double referencing by subtracting 1) Nanobody-HSA dissociation and 2) non-specific binding to reference ligand lane. Binding levels of pre-existing antibodies were determined by setting report points at 125 seconds (5 seconds after end of association). Percentage reduction in pre-existing antibody binding was calculated relative to the binding levels at 125 seconds of a reference NANOBODY®.

Example 1: Production of Representative Glycosylated ISVD's

As representative examples of glycosylated ISVD's of the invention, two variants were made of the serum-albumin binding NANOBODY® of SEQ ID NO: 99. In the first variant (SEQ ID NO:100) an N-glycosylation site (NVT) was provided at positions 108-110 by means of introducing an L108N mutation in the sequence of SEQ ID NO: 99. In the second variant (SEQ ID NO:101, glycosylated reference) an N-glycosylation site (NDT) was provided at positions 85-87 by means of introducing an E85N mutation in the sequence of SEQ ID NO:99. As can be seen, in all three cases the glycosylation site could advantageously be introduced by means of a single amino acid mutation.

The mutations were introduced by suitably changing the codon encoding the relevant amino acid in a nucleotide sequence encoding SEQ ID NO:99 (in practice, the relevant nucleic acid was synthesized de novo using standard nucleic acid synthesis techniques).

The nucleic acid sequences encoding the ISVDs were then expressed in HEK293 cells using a protocol and techniques known per se in the art. The resulting ISVDs were recovered, purified and isolated in a manner known per se.

Example 2: Testing of Representative Glycosylated ISVD's for Binding by Pre-Existing Antibodies Binding of pre-existing antibodies to the ISVDs obtained in Example 1 was tested using essentially the same set of 96 samples of healthy human volunteers as was used in Example 4 (see Table F) from applicant's co-pending US priority application 61/014,015 filed on Jun. 18, 2014 and entitled "Improved immunoglobulin variable domains". The results are shown in Table I

TABLE I

| NANOBODY ® tested on 98 samples (healthy subjects) | | Binding level at 125 seconds <10 RU | Binding level at 125 seconds <20 RU | Binding level at 125 seconds >20 RU |
|---|---|---|---|---|
| SEQ ID NO: 99 | | 17 | 33 | 63 |
| SEQ ID NO: 99 + E85N (comparative) | SEQ ID 101 | 17 | 32 | 64 |
| SEQ ID NO: 99 + L108N (invention) | SEQ ID NO: 100 | 83 | 89 | 7 |

The results are plotted in FIG. 9, with each dot representing a binding value obtained for one of the samples tested against the relevant ISVDs. As can be seen, the preferred glycosylated ISVD of the invention (SEQ ID NO:100) essentially showed major reduction of binding by pre-existing antibodies compared to the reference without the glycosylation site (SEQ ID NO:99) and compared to the comparative glycosylated sequence of SEQ ID NO:101.

To calculate the reduction in binding by pre-existing antibodies (see the following Example 3), for SEQ ID NO: 99 (reference), SEQ ID NO: 100 (invention) and SEQ ID NO:101 (comparative), the average was taken of the RU values measured for the five samples showing the highest RU values for each construct (see the samples indicated with a circle in FIG. 10). The results are mentioned in Table II.

TABLE II

| SEQ ID NO | SEQ ID NO: 99 | SEQ ID NO: 100 (SEQ ID NO: 99 + L108N) | SEQ ID NO: 101 (SEQ ID NO: 99 + E85N) |
|---|---|---|---|
| 1st(*) | 274 | 53 | 283 |
| 2nd | 227 | 36 | 233 |
| 3rd | 215 | 33 | 203 |
| 4th | 183 | 33 | 197 |
| 5th | 173 | 27 | 167 |
| average | 214 | 36 | 217 |

Note:
"1st", "2nd" etc. indicate the highest, second highest, etc. RU value measured for each construct.

As can be see, according to this measurement, introduction of glycosylation of the invention reduced binding by pre-existing antibodies by 73% (100%−(36/214×100%=) 17%) compared to the non-glycosylated reference of SEQ ID NO: 99 and by 73% (100%−(36/217×100%=) 17%) compared to the comparative SEQ ID NO:101.

Example 3: General Method for Determining the Reduction of Binding by Pre-Existing Antibodies To test a VH domain or compound of the invention (i.e. with glycosylation according to the invention) for reduction of binding by pre-existing antibodies (i.e. compared to a reference without said glycosylation), and to determine said reduction, the following methodology can be used.

The VH domain or compound of the invention is tested for binding against a set of (at least) 50 relevant human serum samples (e.g. from healthy volunteers or from a relevant disease population), using the general protocol set out in the introduction to this Experimental Part. The data (RU value measured for each sample) is then collected and the average RU value is calculated for the 5 samples that gave the highest RU value. The same measurement (using the same sample set and same conditions for determining binding) is then repeated for the reference compound, and again the average RU value is calculated for the 5 samples that gave the highest RU value. The difference between these two average RU values is then expressed at a percentage, as follows:

100%−([Average RU value compound to be tested]/ [Average RU value reference]×100%)

in which

"[Average RU value compound to be tested]"=the average RU value calculated for the 5 samples that gave the highest RU value with the compound to be tested; and "[Average RU value reference]"=the average RU value calculated for the 5 samples that gave the highest RU value with the reference.

FIG. 10 schematically shows (based on the data shown in FIG. 9, which is used as an example) how this calculation is made. The samples giving the 5 highest RU values for each of the constructs of SEQ ID NO: 99, SEQ ID NO: 100 and SEQ ID NO:101, respectively, are indicated by circles in each column and are indicated by (1) for the construct of SEQ ID NO: 99 (left hand column) and by (2) for the construct of SEQ ID NO: 100 (middle column). To calculate the reduction of binding by pre-existing antibodies to the construct of SEQ ID NO: 100 compared to the construct of SEQ ID NO:99, the average RU value measured for the five samples with the highest amount of binding (i.e. highest RU values) to SEQ ID NO: 100 is calculated (this is indicated by as "Avg. 2" in FIG. 10 and said average RU value is indicated as (**). Similarly, the average RU value measured for the five samples with the highest amount of binding (i.e. highest RU values) to SEQ ID NO: 99 is calculated (this is indicated by as "Avg. 1" in FIG. 10 and said average RU value is indicated as (*). The reduction in binding for SEQ ID NO:100 compared to SEQ ID NO:99 is then calculated 100%−[(**)/(*)×100%].

Example 2 gives a non-limiting example of how this reduction actually calculated for the data shown in FIG. 9 and Table II based on measured RU values for the relevant samples/constructs.

The invention claimed is:

1. A heavy-chain immunoglobulin single variable domain that consists of formula 1: FR1-CDR1-FR2-CDR2-FR3-CDR3-FR4, wherein FR1 to FR4 refer to framework regions 1 to 4 and CDR1 to CDR3 refer to complementary determining regions 1 to 3, wherein FR1 comprises the amino acid residues at positions 1-30, FR2 comprises the amino acid residues at positions 36-49, FR3 comprises the amino acid residues at positions 66-94, and FR4 comprises the amino acid residues at positions 103-113; and which contains a glycosylation site such that the amino acid residue at one of positions 10, 11, 12, 13, 14, 39, 40, 41, 42, 87, 89, 108, 112, 113 or 114 is or can be glycosylated, wherein the numbering is according to Kabat numbering.

2. The heavy-chain immunoglobulin single variable domain according to claim 1, which contains an N-glycosylation site such that the amino acid residue at one of positions 10, 11, 12, 13, 14, 39, 40, 41, 42, 87, 89, 108, 112, 113 or 114 is an asparagine residue that is or can be N-glycosylated.

3. The heavy-chain immunoglobulin single variable domain according to claim 2 that contains an NXT or NXS motif, in which X can be any amino acid except proline, such that the asparagine (N) residue of the NXT/NXS motif is present at one of positions 10, 11, 12, 13, 14, 39, 40, 41, 42, 87, 89, 108, 112, 113 or 114.

4. The heavy-chain immunoglobulin single variable domain according to claim 1, that is not glycosylated.

5. The heavy-chain immunoglobulin single variable domain according to claim 1, that is glycosylated at one of positions 10, 11, 12, 13, 14, 39, 40, 41, 42, 87, 89, 108, 112, 113 or 114.

6. The heavy-chain immunoglobulin single variable domain according to claim 1, which contains a glycosylation site such that the amino acid residue at one of positions 108, 112, 113 or 114 is or can be glycosylated.

7. The heavy-chain immunoglobulin single variable domain according to claim 6, which contains an N-glycosylation site such that the amino acid residue at one of positions 108, 112, 113 or 114 is an asparagine residue that is or can be N-glycosylated.

8. The heavy-chain immunoglobulin single variable domain according to claim 7 that contains an NXT or NXS motif, in which X can be any amino acid except proline, such that the asparagine (N) residue of the NXT/NXS motif is present at one of positions 108, 112, 113 or 114.

9. The heavy-chain immunoglobulin single variable domain according to claim 6, that is not glycosylated.

10. The heavy-chain immunoglobulin single variable domain according to claim 6, that is glycosylated at one of positions 108, 112, 113 or 114.

11. The heavy-chain immunoglobulin single variable domain according to claim 1, which is or is derived from a variable domain of a camelid heavy chain antibody (VHH), a humanized variable domain of a camelid heavy chain antibody (humanized VHH), a variable domain of a heavy chain of a human antibody (human VH), or a camelized variable domain of the heavy chain of a human antibody (camelized human VH).

12. A protein, polypeptide, construct or other chemical entity that comprises or consists essentially of at least one heavy-chain immunoglobulin single variable domain according to claim 1.

13. The protein or polypeptide of claim 12, wherein the at least one heavy-chain immunoglobulin single variable domain is at the C-terminal end of the protein or polypeptide.

14. A nucleotide sequence or nucleic acid encoding the heavy-chain immunoglobulin single variable domain according to claim 1 or a protein or polypeptide that comprises or consists essentially of at least one heavy-chain immunoglobulin single variable domain according to claim 1.

15. A composition comprising the heavy-chain immunoglobulin single variable domain according to claim 1.

16. The composition according to claim 15, which is a pharmaceutical composition.

17. A heavy-chain immunoglobulin single variable domain that consists of formula 1: FR1-CDR1-FR2-CDR2-FR3-CDR3-FR4, wherein FR1 to FR4 refer to framework regions 1 to 4 and CDR1 to CDR3 refer to complementarity determining regions 1 to 3,
  wherein the heavy-chain immunoglobulin single variable domain forms a single functional antigen binding site; and
  which contains a glycosylation site such that the amino acid residue at one of positions 10, 11, 12, 13, 14, 39, 40, 41, 42, 87, 89, 108, 112, 113 or 114 is or can be glycosylated, wherein the numbering is according to Kabat numbering.

18. A protein, polypeptide, construct or other chemical entity that comprises or consists essentially of at least one heavy-chain immunoglobulin single variable domain according to claim 17.

19. A nucleotide sequence or nucleic acid encoding the heavy-chain immunoglobulin single variable domain according to claim 17 or a protein or polypeptide that comprises or consists essentially of at least one heavy-chain immunoglobulin single variable domain according to claim 17.

20. A composition comprising the heavy-chain immunoglobulin single variable domain according to claim 17.

21. A heavy-chain immunoglobulin single variable domain that consists of formula 1: FR1-CDR1-FR2-CDR2-FR3-CDR3-FR4, wherein FR1 to FR4 refer to framework regions 1 to 4 and CDR1 to CDR3 refer to complementarity determining regions 1 to 3,
  wherein position 11 is V or K; and
  which contains a glycosylation site such that the amino acid residue at one of positions 10, 12, 13, 14, 39, 40, 41, 42, 87, 89, 108, 110, 112, 113 or 114 is or can be glycosylated, wherein the numbering is according to Kabat numbering.

22. A heavy-chain immunoglobulin single variable domain that consists of formula 1: FR1-CDR1-FR2-CDR2-FR3-CDR3-FR4, wherein FR1 to FR4 refer to framework regions 1 to 4 and CDR1 to CDR3 refer to complementarity determining regions 1 to 3, wherein position 14 is P; and which contains a glycosylation site such that the amino acid residue at one of positions 10, 11, 12, 13, 39, 40, 41, 42, 87, 89, 108, 112, 113 or 114 is or can be glycosylated, wherein the numbering is according to Kabat numbering.

23. A heavy-chain immunoglobulin single variable domain that consists of formula 1: FR1-CDR1-FR2-CDR2-FR3-CDR3-FR4, wherein FR1 to FR4 refer to framework regions 1 to 4 and CDR1 to CDR3 refer to complementarity determining regions 1 to 3, wherein position 41 is A; and which contains a glycosylation site such that the amino acid residue at one of positions 10, 11, 12, 13, 14, 39, 40, 42, 87, 89, 108, 112, 113 or 114 is or can be glycosylated, wherein the numbering is according to Kabat numbering.

24. A heavy-chain immunoglobulin single variable domain that consists of formula 1: FR1-CDR1-FR2-CDR2-FR3-CDR3-FR4, wherein FR1 to FR4 refer to framework regions 1 to 4 and CDR1 to CDR3 refer to complementarity determining regions 1 to 3, wherein position 89 is T or L; and which contains a glycosylation site such that the amino acid residue at one of positions 10, 11, 12, 13, 14, 39, 40, 41, 42, 87, 108, 110, 112, 113 or 114 is or can be glycosylated, wherein the numbering is according to Kabat numbering.

* * * * *